(12) United States Patent
Lashinski et al.

(10) Patent No.: US 7,993,397 B2
(45) Date of Patent: Aug. 9, 2011

(54) REMOTELY ADJUSTABLE CORONARY SINUS IMPLANT

(75) Inventors: Randall T. Lashinski, Santa Rosa, CA (US); David Mark Taylor, Lake Forest, CA (US); Richard S. Kusleika, Eden Prairie, MN (US)

(73) Assignee: Edwards Lifesciences AG, Nyon (CH)

( * ) Notice: Subject to any disclaimer, the term of this patent is extended or adjusted under 35 U.S.C. 154(b) by 773 days.

(21) Appl. No.: 10/818,186

(22) Filed: Apr. 5, 2004

(65) Prior Publication Data

US 2005/0222678 A1 Oct. 6, 2005

(51) Int. Cl.
*A61F 2/24* (2006.01)

(52) U.S. Cl. ...................................... 623/2.37; 623/1.11

(58) Field of Classification Search .................. 623/2.11, 623/2.36–2.4, 1.11, 1.23, 13.13–13.16, 23.64–23.65, 623/603–904; 606/191, 192, 194, 198, 232; 604/116, 174, 175
See application file for complete search history.

(56) References Cited

U.S. PATENT DOCUMENTS

| | | | |
|---|---|---|---|
| 3,461,869 A * | 8/1969 | Hargest | 604/175 |
| 4,164,046 A | 8/1979 | Cooley | |
| 4,655,771 A | 4/1987 | Wallsten | |
| 4,954,126 A | 9/1990 | Wallsten | |
| 5,006,106 A | 4/1991 | Angelchik | |
| 5,061,275 A | 10/1991 | Wallsten et al. | |
| 5,064,435 A | 11/1991 | Porter | |
| 5,071,407 A | 12/1991 | Termin et al. | |
| 5,104,404 A | 4/1992 | Wolff | |
| 5,163,955 A | 11/1992 | Love et al. | |
| 5,170,802 A | 12/1992 | Mehra | |
| 5,209,730 A | 5/1993 | Sullivan | |
| 5,224,491 A | 7/1993 | Mehra | |
| 5,304,131 A | 4/1994 | Paskar | |
| 5,382,259 A | 1/1995 | Phelps et al. | |
| 5,383,892 A | 1/1995 | Cardon et al. | |
| 5,390,661 A | 2/1995 | Griffith et al. | |
| 5,441,515 A | 8/1995 | Khosravi et al. | |
| 5,449,373 A | 9/1995 | Pinchasik et al. | |
| 5,476,471 A | 12/1995 | Shifrin et al. | |
| 5,496,275 A | 3/1996 | Sirhan et al. | |

(Continued)

FOREIGN PATENT DOCUMENTS

DE 196 05 042 A1 1/1998

(Continued)

OTHER PUBLICATIONS

Laaksovirta et al., *Expansion and bioabsorption of the self-reinforced lactic and glycolic acid copolymer prostatic spiral stent*, PubMed, Excerpt from J Urol Sep. 2001; 166(3):919-22, one sheet.

(Continued)

*Primary Examiner* — David Isabella
*Assistant Examiner* — Suba Ganesan
(74) *Attorney, Agent, or Firm* — Melinda Michalerya

(57) ABSTRACT

Disclosed are methods and devices for applying pressure to an adjacent tissue structure, such as the annulus of the mitral valve. An adjustable implant is provided with an elongate control line having a distal end connected to the implant and a proximal end spaced apart from the implant. The device enables post implantation adjustment, by accessing the proximal end of the control line and manipulating the control line to adjust the implant.

26 Claims, 22 Drawing Sheets

U.S. PATENT DOCUMENTS

| | | | |
|---|---|---|---|
| 5,531,779 A | 7/1996 | Dahl et al. | |
| 5,534,007 A | 7/1996 | St. Germain et al. | |
| 5,571,135 A | 11/1996 | Fraser et al. | |
| 5,584,879 A | 12/1996 | Reimold et al. | |
| 5,591,197 A | 1/1997 | Orth et al. | |
| 5,593,442 A | 1/1997 | Klein | |
| 5,607,444 A | 3/1997 | Lam | |
| 5,674,280 A | 10/1997 | Davidson et al. | |
| 5,713,949 A | 2/1998 | Jayaraman | |
| 5,741,274 A | 4/1998 | Lenker et al. | |
| 5,817,126 A | 10/1998 | Imran | |
| 5,824,071 A | 10/1998 | Nelson et al. | |
| 5,876,419 A | 3/1999 | Carpenter et al. | |
| 5,876,433 A | 3/1999 | Lunn | |
| 5,891,108 A | 4/1999 | Leone et al. | |
| 5,911,732 A | 6/1999 | Hojeibane | |
| 5,919,233 A | 7/1999 | Knopf et al. | |
| 5,935,081 A | 8/1999 | Kadhiresan | |
| 5,954,761 A | 9/1999 | Machek et al. | |
| 5,980,552 A | 11/1999 | Pinchasik et al. | |
| 6,006,122 A | 12/1999 | Smits | |
| 6,013,854 A | 1/2000 | Moriuchi | |
| 6,019,739 A | 2/2000 | Rhee et al. | |
| 6,027,525 A | 2/2000 | Suh et al. | |
| 6,051,020 A | 4/2000 | Goicoechea et al. | |
| 6,071,292 A | 6/2000 | Makower et al. | |
| 6,077,296 A | 6/2000 | Shokoohi et al. | |
| 6,093,203 A | 7/2000 | Uflacker | |
| 6,110,100 A | 8/2000 | Talpade | |
| 6,123,699 A | 9/2000 | Webster, Jr. | |
| 6,161,029 A | 12/2000 | Spreigl et al. | |
| 6,161,543 A | 12/2000 | Cox et al. | |
| 6,165,169 A | 12/2000 | Panescu et al. | |
| 6,168,619 B1 | 1/2001 | Dinh et al. | |
| 6,171,329 B1 | 1/2001 | Shaw et al. | |
| 6,183,411 B1 | 2/2001 | Mortier et al. | |
| 6,203,556 B1 | 3/2001 | Evans et al. | |
| 6,210,432 B1 | 4/2001 | Solem et al. | |
| 6,221,103 B1 | 4/2001 | Melvin | |
| 6,248,119 B1 | 6/2001 | Solem | |
| 6,250,308 B1 | 6/2001 | Cox | |
| 6,264,602 B1 | 7/2001 | Mortier et al. | |
| 6,264,691 B1 | 7/2001 | Gabbay | |
| 6,325,826 B1 | 12/2001 | Vardi et al. | |
| 6,343,605 B1 | 2/2002 | Lafontaine | |
| 6,350,277 B1 | 2/2002 | Kocur | |
| 6,368,348 B1 | 4/2002 | Gabbay | |
| 6,402,679 B1 | 6/2002 | Mortier et al. | |
| 6,402,680 B2 | 6/2002 | Mortier et al. | |
| 6,402,781 B1 | 6/2002 | Langberg et al. | |
| 6,409,760 B1 | 6/2002 | Melvin | |
| 6,537,314 B2 | 3/2003 | Langberg et al. | |
| 6,569,198 B1 * | 5/2003 | Wilson et al. | 623/2.37 |
| 6,626,899 B2 | 9/2003 | Houser et al. | |
| 6,629,534 B1 | 10/2003 | St. Goar et al. | |
| 6,656,221 B2 | 12/2003 | Taylor et al. | |
| 6,669,687 B1 | 12/2003 | Saadat | |
| 6,676,702 B2 | 1/2004 | Mathis | |
| 6,706,065 B2 | 3/2004 | Langberg et al. | |
| 6,709,456 B2 | 3/2004 | Langberg et al. | |
| 6,764,510 B2 | 7/2004 | Vidlund et al. | |
| 6,790,231 B2 | 9/2004 | Liddicoat et al. | |
| 6,793,673 B2 | 9/2004 | Kowalsky et al. | |
| 6,797,001 B2 | 9/2004 | Mathis et al. | |
| 6,800,090 B2 | 10/2004 | Alferness et al. | |
| 6,810,882 B2 | 11/2004 | Langberg et al. | |
| 6,824,562 B2 | 11/2004 | Mathis et al. | |
| 6,890,353 B2 | 5/2005 | Cohn et al. | |
| 6,908,478 B2 | 6/2005 | Alferness et al. | |
| 6,989,028 B2 | 1/2006 | Lashinski et al. | |
| 6,997,951 B2 | 2/2006 | Solem et al. | |
| 7,011,682 B2 | 3/2006 | Lashinski et al. | |
| 7,044,967 B1 | 5/2006 | Solem et al. | |
| 7,090,695 B2 | 8/2006 | Solem et al. | |
| 2001/0018611 A1 | 8/2001 | Solem et al. | |
| 2001/0044568 A1 | 11/2001 | Langberg et al. | |
| 2002/0016628 A1 | 2/2002 | Langberg et al. | |
| 2002/0019660 A1 | 2/2002 | Gianotti et al. | |
| 2002/0022880 A1 | 2/2002 | Melvin | |
| 2002/0087173 A1 | 7/2002 | Alferness et al. | |
| 2002/0103533 A1 | 8/2002 | Langberg et al. | |
| 2002/0111533 A1 | 8/2002 | Melvin | |
| 2002/0111647 A1 | 8/2002 | Khairkhahan et al. | |
| 2002/0124857 A1 | 9/2002 | Schroeppel | |
| 2002/0151961 A1 | 10/2002 | Lashinski et al. | |
| 2002/0183837 A1 | 12/2002 | Streeter et al. | |
| 2002/0183838 A1 | 12/2002 | Liddicoat et al. | |
| 2002/0183841 A1 | 12/2002 | Cohn et al. | |
| 2002/0188170 A1 | 12/2002 | Santamore et al. | |
| 2003/0078465 A1 | 4/2003 | Pai et al. | |
| 2003/0078654 A1 | 4/2003 | Taylor et al. | |
| 2003/0083538 A1 | 5/2003 | Adams et al. | |
| 2003/0105520 A1 | 6/2003 | Alferness et al. | |
| 2003/0120341 A1 | 6/2003 | Shennib et al. | |
| 2003/0130730 A1 | 7/2003 | Cohn et al. | |
| 2003/0135267 A1 | 7/2003 | Solem et al. | |
| 2003/0144697 A1 | 7/2003 | Mathis et al. | |
| 2003/0171806 A1 | 9/2003 | Mathis et al. | |
| 2003/0204138 A1 | 10/2003 | Choi | |
| 2003/0225454 A1 | 12/2003 | Mathis et al. | |
| 2003/0236569 A1 | 12/2003 | Mathis et al. | |
| 2004/0010305 A1 | 1/2004 | Alferness et al. | |
| 2004/0019377 A1 | 1/2004 | Taylor et al. | |
| 2004/0039443 A1 | 2/2004 | Solem et al. | |
| 2004/0073302 A1 | 4/2004 | Rourke et al. | |
| 2004/0098116 A1 | 5/2004 | Callas et al. | |
| 2004/0102839 A1 | 5/2004 | Cohn et al. | |
| 2004/0102840 A1 | 5/2004 | Solem et al. | |
| 2004/0102841 A1 | 5/2004 | Langberg et al. | |
| 2004/0133192 A1 | 7/2004 | Houser et al. | |
| 2004/0133220 A1 | 7/2004 | Lashinski et al. | |
| 2004/0133240 A1 | 7/2004 | Adams et al. | |
| 2004/0133273 A1 | 7/2004 | Cox | |
| 2004/0138744 A1 | 7/2004 | Lashinski et al. | |
| 2004/0153146 A1 | 8/2004 | Lashinski et al. | |
| 2004/0153147 A1 | 8/2004 | Mathis | |
| 2004/0158321 A1 | 8/2004 | Reuter et al. | |
| 2004/0176840 A1 | 9/2004 | Langberg et al. | |
| 2004/0186566 A1 | 9/2004 | Hindrichs et al. | |
| 2004/0210240 A1 | 10/2004 | Saint | |
| 2004/0220654 A1 | 11/2004 | Mathis et al. | |
| 2004/0220657 A1 | 11/2004 | Nieminen et al. | |
| 2004/0254600 A1 | 12/2004 | Zarbatany et al. | |
| 2004/0267358 A1 | 12/2004 | Reitan | |
| 2005/0004667 A1 | 1/2005 | Swinford et al. | |
| 2005/0010240 A1 | 1/2005 | Mathis et al. | |
| 2005/0021121 A1 | 1/2005 | Reuter et al. | |
| 2005/0027351 A1 | 2/2005 | Reuter et al. | |
| 2005/0043792 A1 | 2/2005 | Solem et al. | |
| 2005/0049681 A1 * | 3/2005 | Greenhalgh et al. | 623/1.15 |
| 2005/0060030 A1 | 3/2005 | Lashinski et al. | |
| 2005/0080483 A1 | 4/2005 | Solem et al. | |
| 2005/0096740 A1 | 5/2005 | Langberg et al. | |
| 2005/0177228 A1 | 8/2005 | Solem et al. | |
| 2006/0116756 A1 | 6/2006 | Solem et al. | |
| 2006/0116757 A1 | 6/2006 | Lashinski et al. | |
| 2006/0184230 A1 | 8/2006 | Solem et al. | |

FOREIGN PATENT DOCUMENTS

| | | |
|---|---|---|
| DE | 196 11 755 A1 | 2/1998 |
| EP | 0 727 239 A2 | 8/1996 |
| WO | WO 95/16407 | 6/1995 |
| WO | WO 96/34211 | 10/1996 |
| WO | WO 96/40356 | 12/1996 |
| WO | WO 98/18411 | 5/1998 |
| WO | WO 98/51365 | 11/1998 |
| WO | WO 99/44534 | 9/1999 |
| WO | WO 99/53977 | 10/1999 |
| WO | WO 00/18320 | 4/2000 |
| WO | WO 00/41649 | 7/2000 |
| WO | WO 00/44313 A1 | 8/2000 |
| WO | WO 01/00111 A1 | 1/2001 |
| WO | WO 01/50985 A1 | 7/2001 |
| WO | WO 01/54618 A1 | 8/2001 |
| WO | WO 01/85061 A2 | 11/2001 |
| WO | WO 01/89426 A1 | 11/2001 |
| WO | WO 02/00099 A2 | 1/2002 |

| | | | |
|---|---|---|---|
| WO | WO 02/01999 A2 | 1/2002 |
| WO | WO 02/05888 A1 | 1/2002 |
| WO | WO 02/34118 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/037171 A2 | 5/2003 |
| WO | WO 2004/019816 A2 | 3/2004 |
| WO | WO 2004/045463 A2 | 6/2004 |
| WO | WO 2004/084746 A2 | 10/2004 |

OTHER PUBLICATIONS

Liu et al., *Sutural expansion osteogenesis for management of the bony-tissue defect in cleft palate repair: experimental studies in dogs*, PubMed, Excerpt from Plast Reconstr Surg May 2000; 105(6):2012-25; discussion 2026-7, two sheets.

Yoneyama et al., *Super-elastic property of Ti-Ni alloy for use in dentistry*, PubMed, Excerpt from Front Med Biol Eng 2000; 10(2):97-103, one sheet.

Kotian, *Shape memory effect and super elasticity it's dental applications*, PubMed, Excerpt from Indian J Dent Res Apr.-Jun. 2001; 12(2):101-4, one sheet.

Kuo et al., *The use of nickel-titanium alloy in orthopedic surgery in China*, PubMed, Excerpt from Orthopedics Jan. 1989; 12(1):111-6, one sheet.

Civjan et al., *Potential applications of certain nickel-titanium (nitinol) alloys*, PubMed, Excerpt from J Dent Res Jan.-Feb. 1975;54(1):89-96, one sheet.

Brennan, *Suite of Shape-Memory Polymers*, http:///pubs.acs.org/cen/topstory/7906/7906notw1.html, News of the Week Materials, Feb. 5, 2001, vol. 79, No. 6, Cenear 79 6 pp. 5, ISSN 0009-2347, three sheets.

Stikeman, *Total Recall*, AN MIT Enterprise Technology Review—Innovation, Jun. 2001, two sheets.

European Patent Office Office action dated Dec. 22, 2003 for Application No. 00 946 661.6-2310, 4 sheets.

Written Opinion dated Nov. 8, 2002 for International application No. PCT/EP01/10371, 14 sheets.

International Search Report dated Apr. 23, 2002 for International application No. PCT/EP01/10371, 4 sheets.

International Search Report dated Mar. 15, 2000 for National application No. SE 9902455-6, 3 sheets.

International Search Report dated Oct. 9, 2002 for National application No. SE 0200073-5, 5 sheets.

International Search Report dated Jun. 5, 2003 for International application No. PCT/EP 02/14655, 7 sheets.

Buchanan et al., Circumferential Suture of the Mitral Annulus for Correction of Mitral Regurgitation in Dogs, Veterinary Surgery, 27: 182-193, 1998.

Buchanan et al., Sanunarco CD, Circumferential Suture of the Mitral Annulus for Correction of Mitral Regurgitation in Dogs, PubMed, Excerpt from Vet Surg May-Jun. 1998; 27(3): 183-93, abstract, one sheet.

* cited by examiner

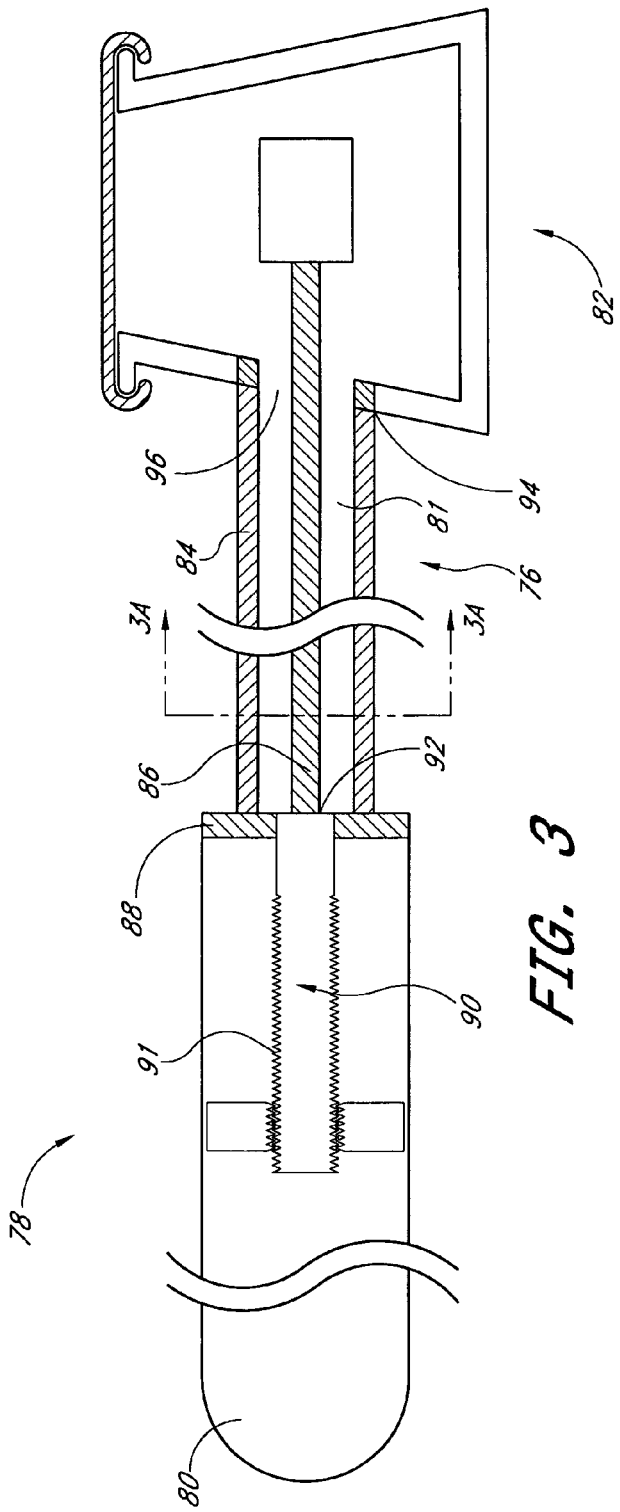
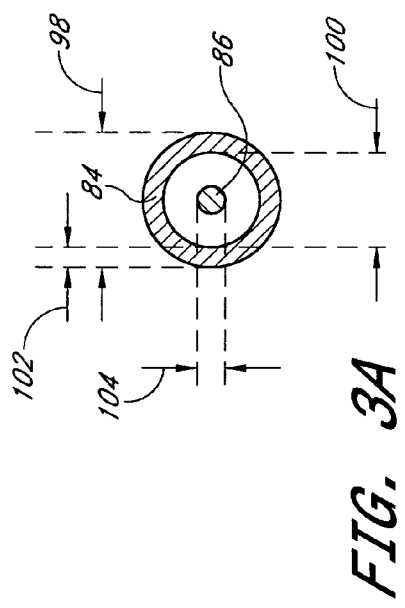
FIG. 3
FIG. 3A

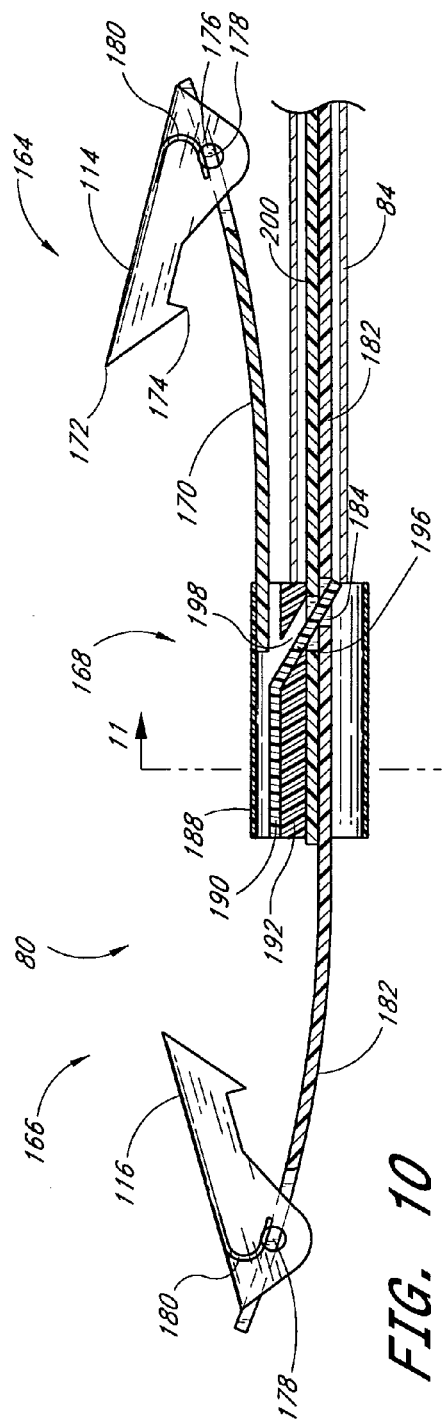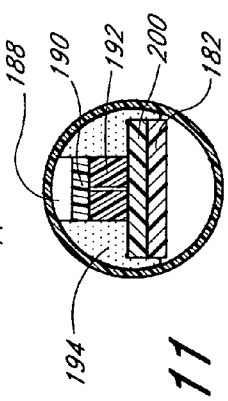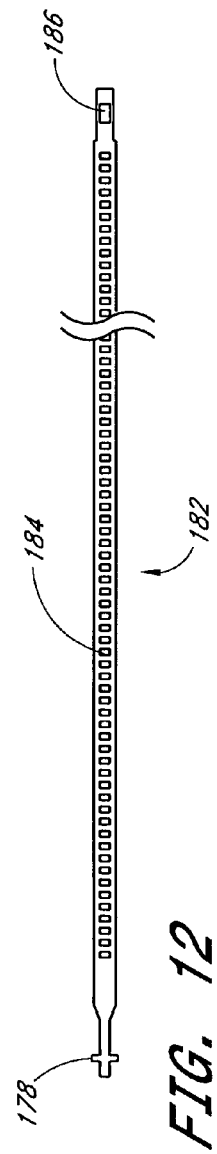
FIG. 10
FIG. 11
FIG. 12

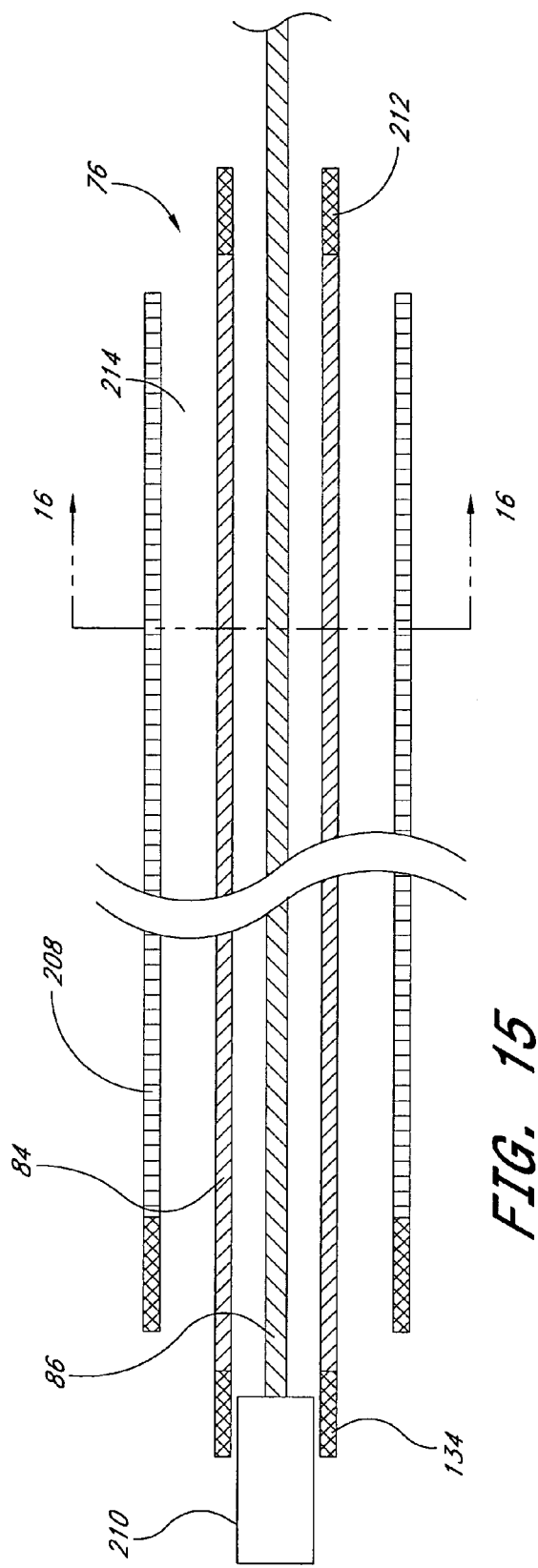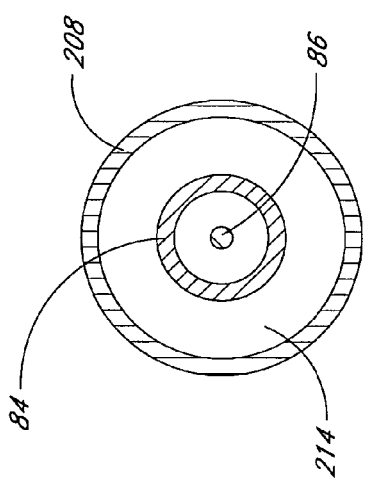
FIG. 15
FIG. 16

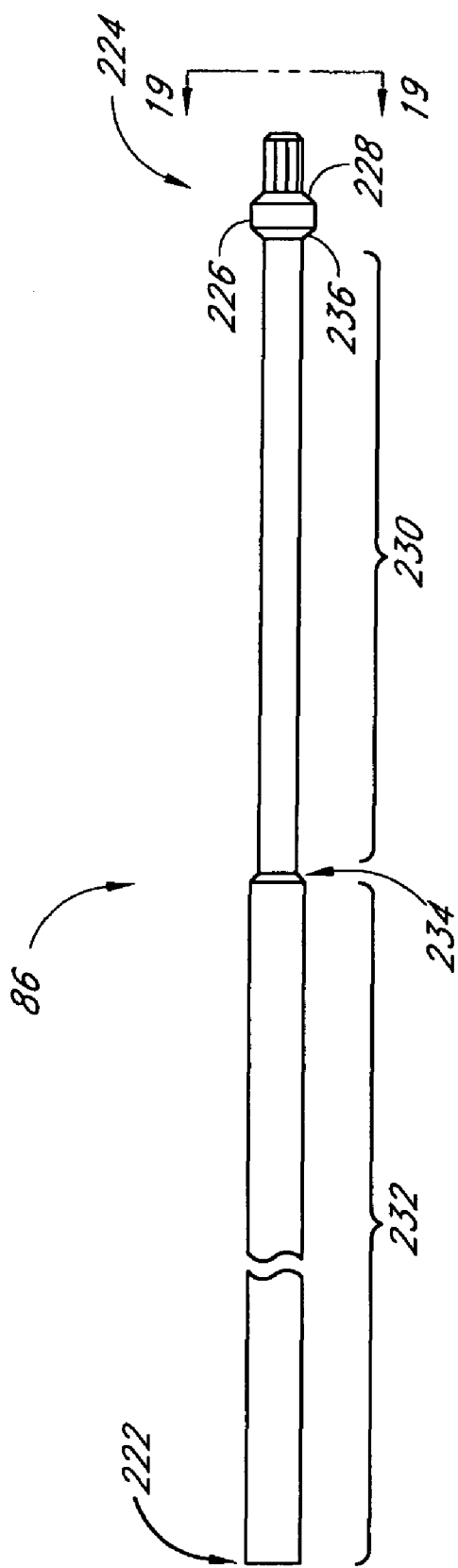
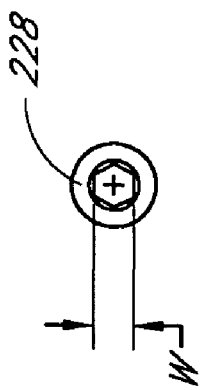
FIG. 18
FIG. 19

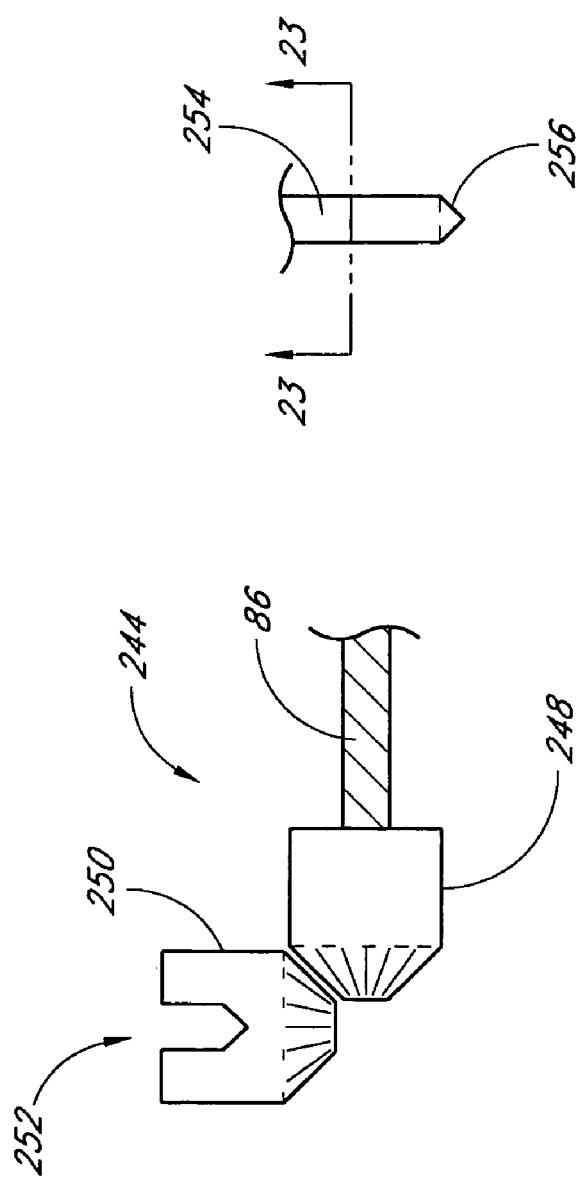

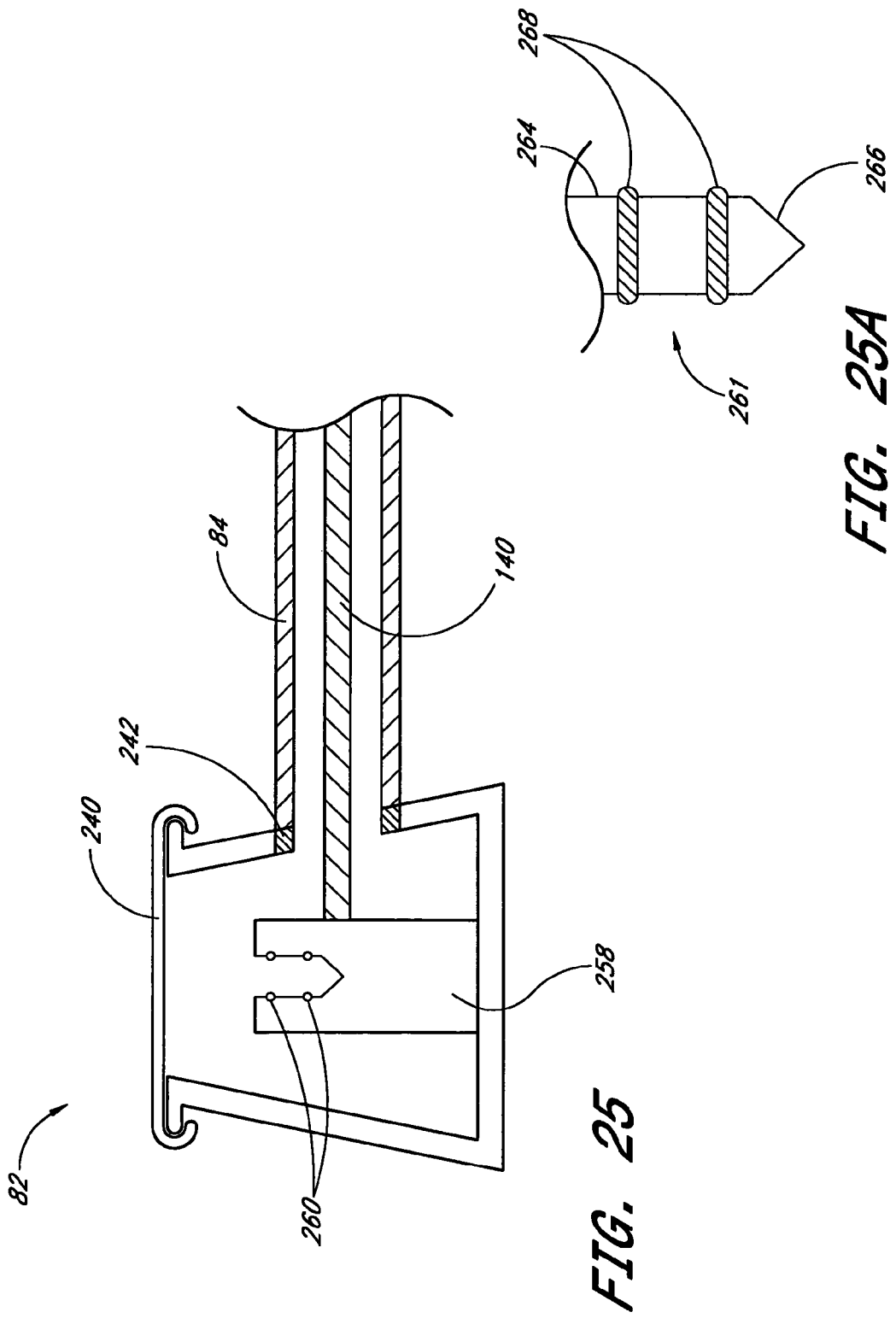

REMOTELY ADJUSTABLE CORONARY SINUS IMPLANT

BACKGROUND OF THE INVENTION

1. Field of the Invention

The present invention relates to intravascular prostheses for remodeling an extravascular anatomical structure. In one application, the present invention relates to a mitral annuloplasty device which is transluminally implantable in the coronary sinus, and is remotely adjustable and/or readjustable post-implantation.

2. Description of the Related Art

Dilated cardiomyopathy occurs as a consequence of many different disease processes that impair myocardial function, such as coronary artery disease and hypertension. The left ventricle enlarges and the ejection fraction is reduced. The resulting increase in pulmonary venous pressure and reduction in cardiac output cause congestive heart failure. Enlargement of the mitral annulus and left ventricular cavity produce mitral valvular insufficiency. This in turn, causes volume overload that exacerbates the myopathy, leading to a vicious cycle of progressive enlargement and worsening mitral regurgitation.

According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques have been developed to repair a diseased or damaged valve. One repair technique which has been shown to be effective in treating incompetence, particularly of the mitral and tricuspid valves, is annuloplasty, in which the effective size of the valve annulus is contracted by attaching a prosthetic annuloplasty ring to the endocardial surface of the heart around the valve annulus. The annuloplasty ring comprises an inner substrate of a metal such as stainless steel or titanium, or a flexible material such as silicone rubber or Dacron cordage, covered with a biocompatible fabric or cloth to allow the ring to be sutured to the heart tissue. The annuloplasty ring may be stiff or flexible, may be split or continuous, and may have a variety of shapes, including circular, D-shaped, C-shaped, or kidney-shaped. Examples are seen in U.S. Pat. Nos. 4,917,698, 5,061,277, 5,290,300, 5,350,420, 5,104,407, 5,064,431, 5,201,880, and 5,041,130, which are incorporated herein by reference.

Annuloplasty rings may also be utilized in combination with other repair techniques such as resection, in which a portion of a valve leaflet is excised, the remaining portions of the leaflet are sewn back together, and a prosthetic annuloplasty ring is then attached to the valve annulus to maintain the contracted size of the valve. Other valve repair techniques in current use include commissurotomy (cutting the valve commissures to separate fused valve leaflets), shortening mitral or tricuspid valve chordae tendonae, reattachment of severed mitral or tricuspid valve chordae tendonae or papillary muscle tissue, and decalcification of the valve leaflets or annulus. Annuloplasty rings may be used in conjunction with any repair procedures where contracting or stabilizing the valve annulus might be desirable.

Although mitral valve repair and replacement can successfully treat many patients with mitral valvular insufficiency, techniques currently in use are attended by significant morbidity and mortality. Most valve repair and replacement procedures require a thoracotomy, usually in the form of a median sternotomy, to gain access into the patient's thoracic cavity. A saw or other cutting instrument is used to cut the sternum longitudinally, allowing the two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, to arrest cardiac function. The patient is placed on extracorporeal cardiopulmonary bypass to maintain peripheral circulation of oxygenated blood.

Of particular interest in the present application are techniques for the repair and replacement of the mitral valve. The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into an anterior position. An opening, or atriotomy, is then made in the right side of the left atrium, anterior to the right pulmonary veins. The atriotomy is retracted by means of sutures or a retraction device, exposing the mitral valve adjacent to the atriotomy. One of the previously identified techniques may then be used to repair or replace the valve.

An alternative technique for mitral valve access has been used when a median sternotomy and/or rotational manipulation of the heart are inappropriate. In this technique, a thoracotomy is made in the right lateral side of the chest, usually in the region of the fourth or fifth intercostal space. One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for cannulation of the aorta and/or coronary arteries to induce cardioplegia, manipulation of surgical instruments, removal of excised tissue, and introduction of an annuloplasty ring or a replacement valve through atriotomy for attachment within the heart.

Mitral valve surgery, including mitral annuloplasty, is usually applied to patients with intrinsic disease of the mitral apparatus. As described, above, these patients may have scarring, retraction, tears or fusion of valve leaflets as well as disorders of the subvalvular apparatus. Definitive repair requires direct visualization of the valve.

Patients who develop mitral regurgitation as a result of dilated cardiomyopathy do not always have intrinsic mitral valve disease. Regurgitation occurs as the result of the leaflets being moved back from each other by the dilated annulus. The ventricle enlarges and becomes spherical, pulling the papillary muscles and chordae away from the plane of the valve and further enlarging the regurgitant orifice. In these patients, correction of the regurgitation does not require repair of the valve leaflets themselves, but simply a reduction in the size of the annulus and the sphericity of the left ventricle.

Mitral annuloplasty without repair of the leaflets or chordae has been shown to be effective in patients with dilated cardiomyopathy who are refractory to conventional medical therapy. Dr. Steve Bolling, at The University of Michigan and coworkers have operated on a cohort of such patients with New York Heart Association Class III and IV symptoms. Average symptom severity decreased from 3.9 preoperatively to 2.0 after surgery. Hemodynamics and ejection fraction improved significantly. Other investigators have achieved similar results as well. However, the morbidity, risks and expense of surgical annuloplasty are very high in patients with cardiomyopathy and congestive heart failure. Thus, a variety of new techniques for the treatment of congestive heart failure are being explored as adjuncts to drug therapy.

Several cardiac restraint devices have been described. U.S. Pat. No. 5,702,343 to Alferness discloses a cardiac reinforcement device that is applied as a jacket over the epicardium in order to limit diastolic expansion. However, this requires an open chest operation to implant and does not directly affect the diameter of the mitral annulus. Another approach is disclosed in U.S. Pat. No. 5,961,440 to Schweich, et al., in which tension members are placed through opposite walls of the heart such that they span the ventricle. Less invasive and "minimally" invasive techniques for valve repair and replacement continue to evolve, both on a stopped heart and on a beating heart. These techniques may provide some benefits over open chest procedures, but they are still attended by significant morbidity and mortality risks.

A need therefore remains for methods and devices for treating mitral valvular insufficiency, or improper functioning of other valves in the heart which are attended by significantly lower morbidity and mortality rates than are the current techniques, and therefore would be well suited to treat patients with dilated cardiomyopathy. Optimally, the procedure can be accomplished through a percutaneous, transluminal approach, using simple, implantable devices which do not depend upon prosthetic valve leaflets or other moving parts.

SUMMARY OF THE INVENTION

There is provided in accordance with one aspect of the present invention, an implant for applying controlled compression against an adjacent tissue structure. The implant comprises an elongate body, having a proximal end and a distal end. The elongate body is moveable between a first configuration in which the body is flexible such as to enable transluminal delivery to a treatment site, and a second configuration for applying pressure to an adjacent tissue structure. The body is coupled to an elongate flexible control line, having a first end attached to the body, and a second end having a coupling thereon. The coupling is adapted to removably receive an adjustment tool, such as a rotatable driver.

In one implementation of the invention, the device is dimensioned for transluminal advancement and positioning within the coronary sinus. The elongate flexible control line is dimensioned to position the coupling at a site near the surface of the skin. Manipulation of the adjustment tool when coupled to the connector adjusts pressure exerted by the implant on adjacent tissue, such as the posterior leaflet of the mitral valve.

In accordance with another aspect of the present invention, there is provided a method of providing a therapeutic compressive force against a tissue structure which is adjacent an implant. The method comprises the steps of positioning a device at a target site in a patient, the device connected by an elongate flexible control line to a remote connector. An adjustment tool is connectable to the connector, and may be actuated cause a portion of the device to move, thereby exerting force against the adjacent tissue structure. The positioning step may be accomplished translumenally, in an open surgical procedure or less invasively through an artificial tissue tract. Translumenal access may be accomplished through a vein, such as one of the internal jugular, subclavian, or femoral veins.

The method may additionally comprise the steps of measuring hemodynamic function prior to, during and/or following the actuating step. The method may additionally comprise the step of determining an ongoing drug therapy, taking into account the post implantation hemodynamic function.

In accordance with a further aspect of the present invention, there is provided a method of treating a patient by accessing and adjusting a previously positioned implant. The method comprises the steps of accessing a connector which is connected to an implant by an elongate control line. An adjustment tool is connected to the connector. The adjustment tool is actuated to adjust an amount of force exerted by the implant against an adjacent tissue. The actuating step may adjust force against a heart valve, such as the mitral valve. In one implementation, the adjustment increases or decreases the pressure on the posterior leaflet of the mitral valve. The accessing a connector step may be accomplished at least ten minutes, and in certain instances at least 24 hours, two weeks, at least a month, at least a year, or five years or more following initial positioning of the implant.

In accordance with another aspect of the present invention, there is provided a medical apparatus for remodeling a mitral valve annulus adjacent the coronary sinus. The apparatus comprises an elongate body, having a proximal end and a distal end. The elongate body is movable between a first configuration for translumenal delivery to a location in or adjacent the heart, such as within at least a portion of the coronary sinus, and a second configuration for remodeling the mitral valve annulus. An elongate flexible control line is attached at a first end to the elongate body, and is provided with a second, free end. Manipulation of the control line adjusts the elongate body between the first transluminal delivery configuration and the second remodeling configuration, or from a first remodeling configuration to a second remodeling configuration.

In one embodiment, the elongate body comprises a tube having a plurality of transverse slots. The elongate body may form an arc when in the remodeling configuration, such as by changing the shape of the slots.

In one implementation, the apparatus is moveable between the implantation configuration and a remodeling configuration in response to proximal retraction of a portion of the control line. Movement between the implantation configuration and remodeling configuration may also be accomplished in response to rotation of at least a portion of the control line.

The implant may additionally comprise at least one anchor, for retaining the apparatus at a deployment site within a vessel. The anchor may comprise a friction enhancing surface structure for engaging the wall of the vessel, and/or at least one barb for piercing the wall of the vessel.

The free end of the control line may be provided with a releasable coupling, for engaging an adjustment tool. The coupling may be provided a barrier, such as a snap fit cap, peelable membrane or pierceable septum, to isolate the coupling from tissue while the free end is subcutaneously implanted within the patient.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 3 is a cross-sectional view of a mitral annuloplasty system used to deliver a mitral annuloplasty device to the coronary sinus of FIG. 2 in accordance with one embodiment of the present invention.

FIG. 3A is a cross-sectional view of the mitral annuloplasty system of FIG. 3 taken along line 3A-3A.

FIG. 10 shows a cross-sectional view of the mitral annuloplasty device of FIG. 6.

FIG. 11 shows the cross-sectional view along line 11-11 of FIG. 10.

FIG. 12 shows the distal ribbon of FIG. 10.

FIG. 15 shows a simplified cross-sectional view of a deployment catheter in accordance with one embodiment of the present invention.

FIG. 16 shows a cross-sectional view of the deployment catheter of FIG. 15 taken along line 16-16.

FIG. 18 is a plan view of a rotational core or driver of a deployment catheter in accordance with another embodiment of the present invention.

FIG. 19 is an end elevational view of a hex-shaped distal end of the driver of FIG. 18 taken along line 19-19.

FIG. 21 is a cross-sectional view of one embodiment of the torque coupling of FIG. 20.

FIG. 22 is a side elevational view of an adjustment tool suitable to engage the torque coupling of FIG. 21.

FIG. 23 is a cross-sectional view of the adjustment tool of FIG. 22 taken along line 23-23.

FIG. 25 is another embodiment of the implantable connector housing, configured to electrically couple a probe to the electrical implant.

FIG. 25A is a side elevational schematic view of the distal end of an electrical connector probe for use with the implantable housing of FIG. 25.

DETAILED DESCRIPTION OF THE PREFERRED EMBODIMENT

Figures 1A, 1B:
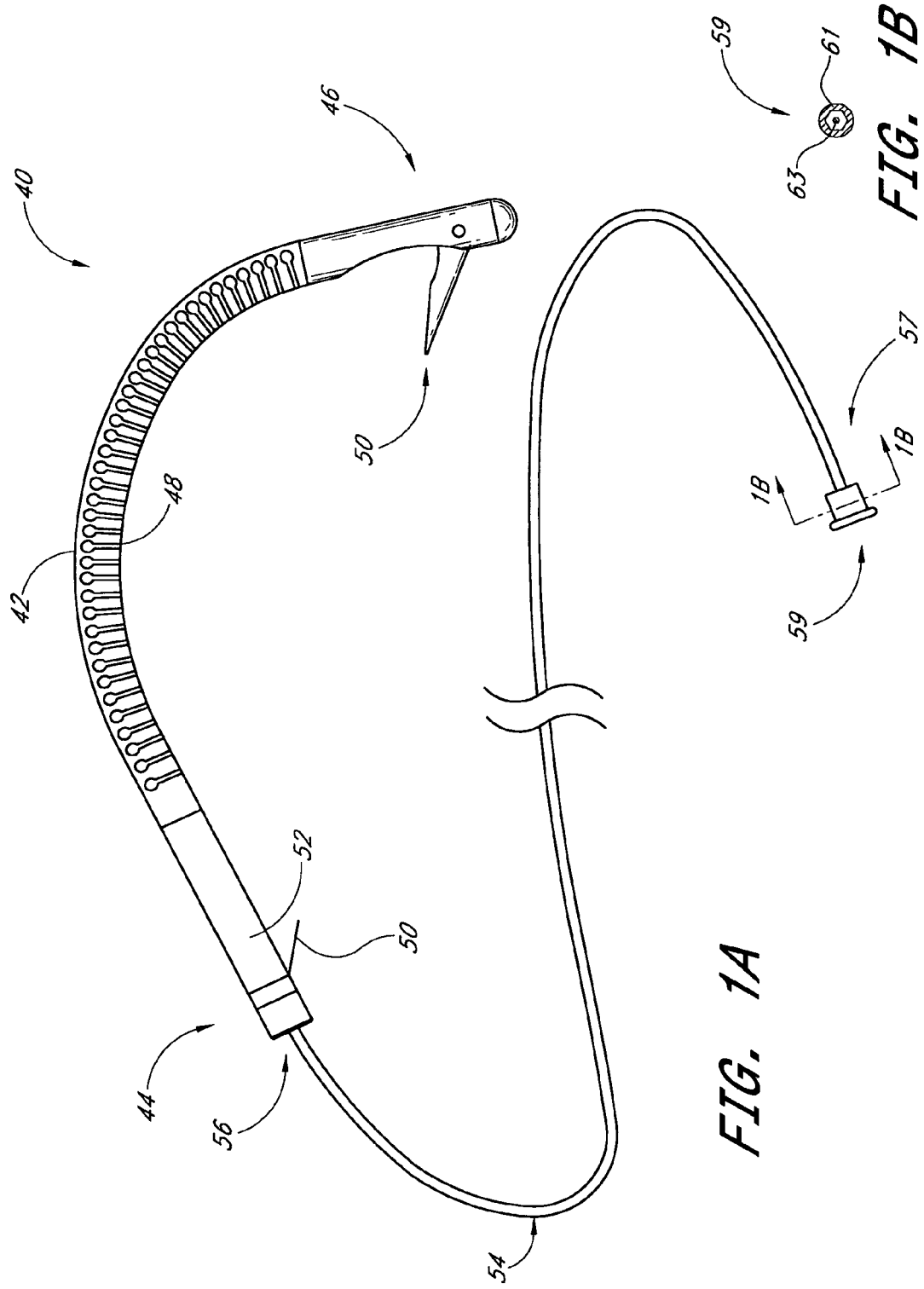
FIG. 1A is a schematic illustration of a mitral annuloplasty system of the present invention having an implant and a remote connector.
FIG. 1B is a cross section taken along the line 1B-1B in FIG. 1A.

The present invention includes methods and apparatus for performing mitral annuloplasty and/or remodeling of the left ventricle using a device that may be introduced surgically or translumenally, and placed within the coronary venous system of the heart. The device may be configured to exert compressive force on the mitral annulus and/or on the left ventricle, reducing the severity of mitral regurgitation and the size of the left ventricular cavity. In one implementation, the device can be used to move the posterior leaflet of the mitral valve anteriorly. The device thus enables treatment of various cardiomyopathies without the morbidity and mortality associated with open chest surgery. Additional details are disclosed in U.S. application Ser. No. 10/066,302, filed on Jan. 30, 2002, and U.S. application Ser. No. 10/634,655, filed Aug. 5, 2003, the disclosures of which are incorporated in their entireties herein by reference.

Subsequent to implanting such an implantable device, mitral valve performance may be monitored in order to determine whether further intervention is indicated. The degree of mitral regurgitation may be monitored such as by transesophageal echo cardiography, intracardiac echo cardiography, fluoroscopy using radiocontrast in the left ventricle (LV-gram), or left atrial or pulmonary capillary wedge pressure tracings, as are understood in the art, during the incremental restriction of the mitral annulus and/or left ventricle step. Monitoring may occur immediately post-implantation, or months or years later during follow-up examinations. While monitoring, it may become apparent that the implantable device's shape or location could be adjusted to improve or resist further degradation of mitral valve performance. The device may then be re-adjusted post implantation if desirable to accommodate post implantation remodeling or other changes which cause a drift in performance of the device.

The present inventors have determined that the coronary sinus and veins provide an ideal conduit for the positioning of an intravascular prosthesis, or implant, for remodeling the mitral annulus, since they are positioned adjacent the mitral annulus and interventricular septum. As used herein, the term "implant" is a broad term, and should not be limited to a permanently introduced structure or device, but could additionally be a temporarily introduced device. The coronary sinus is contained within the atrioventricular groove, and is in close proximity to the posterior, lateral and anterior aspects of the mitral annulus. The coronary sinus and coronary veins are cannulated currently during any of a variety of percutaneous transvenous diagnostic and therapeutic procedures. Permanent placement of pacemaker and defibrillator leads within the coronary sinus and veins is both safe and well tolerated.

The annuloplasty system consists of several components. Desirably, there is a delivery system intended to be introduced percutaneously into a central vein such as the internal jugular, subclavian or femoral veins to access the coronary sinus. The implant of the present invention is deployed from the delivery system, preferably a delivery catheter, into the coronary venous system or into a position within or adjacent the myocardium, to influence the annulus of the mitral valve. Additional tools may be placed through or along the delivery catheter to position the device, apply elements in place, and to control tensioning of the device from the delivery system, as will be discussed in detail below. In an embodiment adapted for post implantation adjustment, a control line may be left behind, extending from the implant to a more easily reached location such as on or just below the skin.

Referring to FIGS. 1A and 1B, there is illustrated a schematic view a remotely adjustable coronary sinus implant in accordance with one aspect of the present invention.

Although the present invention will be described primarily in the context of a coronary sinus implant for influencing the orientation or configuration of the mitral valve annulus, the methods and devices of the present invention may be readily adapted for use in other anatomical locations in the body as will be apparent to those of skill in the art in view of the disclosure herein. In general, the present invention relates to a device for imparting physical force (e.g. compression, tension, expansion etc.) on tissue at a treatment site, wherein the force may be adjusted by manipulation of a control positioned at a site which is remote from the treatment site. This may be particularly desirable where direct access to the treatment site is attended by an undesirable level of morbidity or mortality risk, compared to the risks of accessing the remote site. In general, the remote site may be positioned near the skin.

For certain types of implants or certain types of patients, the ability to access the adjustability feature may only be desired for a relatively short period of time. The proximal end of the remote connector may in these patients extend through the skin and be exposed outside of the patient. Alternatively, in applications where the ability to post adjust the implant may be desirable for extended periods of time such as months or years following implantation, the proximal connector may be implanted subcutaneously at a location where it can be readily located and accessed at a later time.

In general, the coronary sinus implant system comprises an implant 40 having a flexible body 42 extending between a proximal end 44 and a distal end 46. In the illustrated embodiment, the flexible body 42 is provided with a plurality of transverse slots 48, to affect the bending characteristics of the device. Additional device designs and configurations are discussed in detail below.

The implant 40 may be provided with one or two or more tissue anchors 50, which may comprise tissue piercing barbs. Tissue anchor 50 may be actively deployable and retractable in response to the shape of the implant and/or manipulation of a control.

The implant 40 is additionally provided with a control mechanism 52. In general, control mechanism 52 converts a signal or force carried by control line 54 into lateral bending of at least a portion of the implant 40. Details of the control mechanism are discussed below.

The implant 40 is accessible remotely by way of an elongate flexible control line 54. Control line 54 is attached at a distal point of attachment 56 to the implant 40. A proximal end 57 of the control line 54 is provided with a connector 59, such as for subcutaneous placement. Connector 59 is provided with any of a variety of connecting structures which correspond to the nature of the energy or force to be transmitted through the control line 54. For example, referring to FIG. 1B, the connector 59 may comprise a housing 61 which may be a luer type connector having a rotationally keyed core wire 63 or recess connected with a rotatable wire extending throughout the length of the control line 54.

The system may additionally comprise a deployment catheter, for releasably carrying the implant 40 to a target site in the body. The deployment catheter may thereafter be released from the implant 40, and removed from the patient. The control line 54 may be permanently connected to the implant 40, and may extend proximally along side the deployment catheter, or through a lumen in a deployment catheter during deployment. Removal of the deployment catheter may then be accomplished while leaving the control line 54 in place.

In an alternate configuration, the control line 54 may be connected at the distal point of attachment 56 to the implant 40 following positioning of the implant 40 at the treatment site. This may be accomplished by providing an exchange catheter, coupling the exchange catheter to the implant 40 alongside, over or through the deployment catheter, removing the deployment catheter, coupling the control line 54 to the implant 40, and thereafter removing the exchange catheter.

Various aspect of the foregoing will be discussed in greater detail below.

Figure 2:
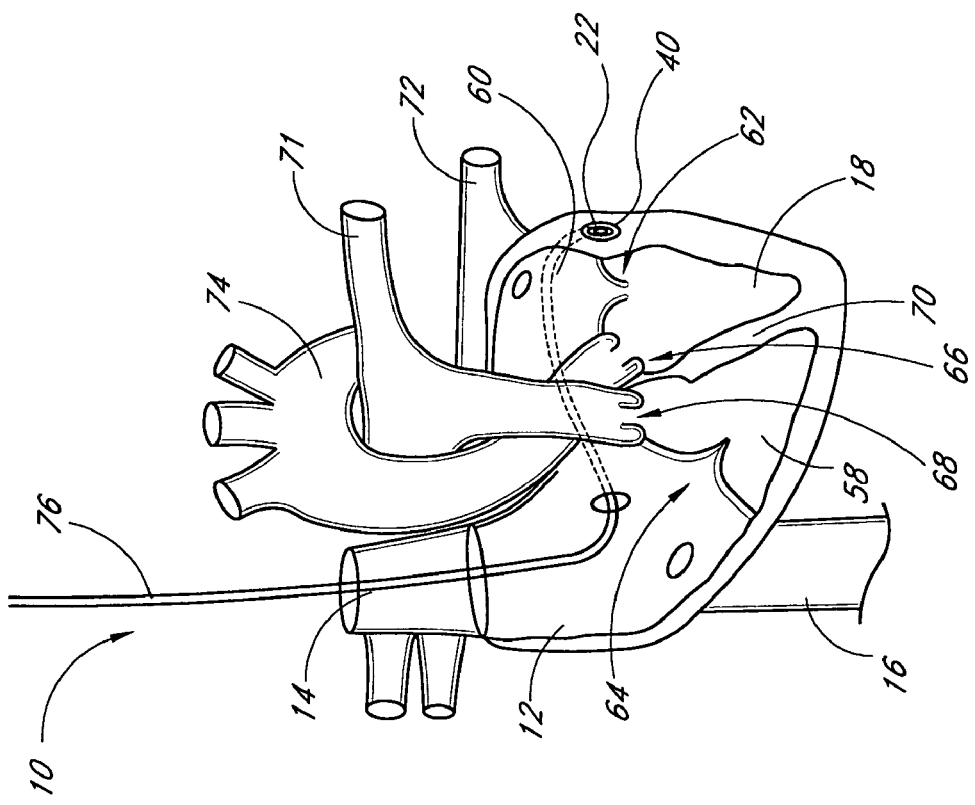
FIG. 2 is a cross-sectional schematic view of a heart showing the relative locations of the coronary sinus and the mitral valve.

Referring to FIG. 2, there is provided a partial cross sectional view of a heart 10. The heart 10 includes four chambers, known as the right atrium 12, right ventricle 58, left atrium 60, and left ventricle 18. The heart 10 also includes four valves, known as the mitral valve 62, tricuspid valve 64, aortic valve 66, and pulmonary valve 68. A septum 70 extends along a longitudinal axis of the heart 10, and separates the right atrium 12 and right ventricle 58 from the left atrium 60 and left ventricle 18.

Deoxygenated blood enters the right atrium 12 of the heart 10 from the upper extremities via the superior vena cava 14 and from the lower extremities via the inferior vena cava 16. As the heart 10 beats, deoxygenated blood is pumped from the right atrium 12 through the tricuspid valve 64 and into the right ventricle 58. From the right ventricle 58 the deoxygenated blood is pumped through the pulmonary valve 68 to the lungs via the pulmonary arteries 71. After the lungs oxygenate the blood, it returns to the left atrium 60 of the heart 10 via the pulmonary veins 72. As the heart 10 beats, the oxygenated blood is pumped from the left atrium 60 through the mitral valve 62 and into the left ventricle 18. From the left ventricle 18, the oxygenated blood is pumped through the aortic valve 66 to the aorta 74, where it is distributed throughout the rest of the body.

The coronary sinus 22 is located towards the outside surface of the heart 10, near the mitral valve 62. A mitral annuloplasty device 40 may be inserted inside of the coronary sinus 22, and an elongate, flexible control line or tether 76 may be routed from the mitral annuloplasty and cardiac reinforcement device 40 to an access location (not shown) positioned near the surface of the patient's body, underneath or above the skin. Other annuloplasty devices, such as those described in greater detail below with respect to FIGS. 4-14, may be implanted within the coronary sinus 22 as well.

Referring now to FIG. 3, there is shown a readjustable mitral annuloplasty system 78 in accordance with the present invention. The readjustable mitral annuloplasty system 78 includes an implant 80, a tether 84, and an implantable connector housing 82. The implant 80 is dimensioned for delivery to a location inside of the body, such as, the coronary sinus 22 of the heart 10 (not shown). The tether 84 couples the implant 80 to the connector housing 82, which may be located near the surface of the patient, in one embodiment just underneath the skin.

The implant 80 may be any of the mitral annuloplasty and/or cardiac reinforcement devices described elsewhere herein. However, the implant 80 can also be a variety of structures suitable for implantation within the body and configured to apply force or restraint on an adjacent tissue structure. Additional implants suitable for implantation within the coronary sinus 22 have been disclosed in U.S. application Ser. No. 10/634,655, filed Aug. 5, 2003, titled, "METHODS AND APPARATUS FOR REMODELING AN EXTRAVASCULAR TISSUE STRUCTURE," hereby incorporated by reference in its entirety.

In one embodiment, in which the implant is adjustable in response to rotation of a portion of the drive mechanism, the tether 76 includes a torque sheath 84 having at least one elongate lumen 81 for moveably carrying torque wire 86. The torque wire 86 extends throughout the axial length of the torque sheath 84, and is able to rotate with respect to the torque sheath 84. The distal end of the torque sheath is attached to the implant 80 at a distal coupling 88 generally on the proximal end of the implant. In one embodiment, the distal coupling 88 is a mechanical bond, such as a compression fitting, a nut, or a lock. Alternatively, the distal coupling 88 can be a chemical bond, such as an adhesive, or a thermal bond, such as that which results from laser or traditional welding. Distal coupling 88 can be any of a variety of mechanisms known to those of skill in the art suitable for attaching the torque sheath 84 to the implant 80, taking into consideration the materials and structures of the implant 80 and torque sheath 84.

The sheath 84 may be formed by any of a variety of techniques well known in the catheter body art, such as extrusion of materials including PEBAX, PEEK, medium and high density polyethylene, polyurethane, and others known in the art. The sheath may also include silicone. Alternatively, the sheath 84 can be constructed from various components or subassemblies. In an embodiment having a rotational torque wire, the sheath 84 preferably exhibits sufficient torque transmission characteristics that it will restrain the implant from rotating, during rotation of the rotatable torque wire. In an embodiment in which, for example, the control wire is a pull wire such that, for example, proximal retraction of the pull wire advances the implant into the remodeling configuration, the sheath 84 preferably has sufficient column strength or pushability to resist collapse while the pull wire is under tension. Catheter wall structures for increasing compression strength and torque transmission are well understood in the medical catheter arts.

Torque transmission in a tubular catheter body can be increased by providing one or more spiral elements within the tubular wall. A polymeric ribbon such as PET, Polyimide, or others may be helically wound around a mandrel, or around an inner tubular layer, with one or more outer tubular layers heat shrunk or coextruded thereon. Alternatively, the wall may be provided with a helical metal element such as a spring, a braided metal structure, or hypodermic needle tubing with a spiral cut. Suitable metals include, among others, stainless steel or nickel titanium alloys.

When made from a spiral cut tube of metal, the torque sheath 84 may be covered over its outside surface, inside surface, or both, with a suitable sleeve. In one embodiment, the sleeve is made from a heat shrinkable material such as a polyethylene. The torque sheath 84 may alternatively be constructed with woven or braided tubular walls. The wall thickness of the completed torque sheath 84 is selected to provide adequate torque, and will vary depending upon the material selected, and the torque sheath length. The torque sheath 84 wall may include multiple layers of torque transmission materials, such as spiral cut tubes, helical wraps or braided or woven structures depending upon the desired dimensions and torque transmission characteristics.

Referring to FIG. 3A, the torque sheath 84 may have an outside diameter 98 in the range of between about 0.010" and about 0.120", sometimes between about 0.015" and about 0.040", and in one embodiment, the diameter is about 0.030". The torque sheath inside diameter 100 is generally in the range of between about 0.010" and about 0.045", sometimes between about 0.015" and about 0.040", and in one embodiment, the diameter is about 0.025". The torque sheath wall thickness 102 is generally in the range of between about 0.001" to about 0.010", sometimes between about 0.002" and 0.008", and in one embodiment, the wall thickness 102 is about 0.005". The torque wire 86 has an outside diameter 104 generally in the range of between about 0.005" to about 0.045", sometimes between about 0.010" to about 0.040", and in one embodiment, the torque wire outside diameter 104 is about 0.020".

The axial length of the tubular sheath 84 can vary widely, depending upon the desired treatment site, and the distance and pathway between the treatment site and the desired location of the proximal connector 59. In general, as will be described below, the pathway of the tubular sheath 84 may conveniently follow the transluminal pathway to implant the remodeling device. The proximal connector 59 may be conveniently positioned in the vicinity of the percutaneous or cutdown access site into the vasculature for the initial implantation.

Accordingly, in a system intended for use in the coronary sinus and implanted by way of the femoral vein, the tubular sheath 84 will generally have a length within the range of from about 80 cm to about 140 cm for a human adult. In a device intended for implantation in the coronary sinus by way of the subclavian vein, the tubular sheath 84 will generally have a length within the range of from about 35 cm to about 55 cm. For an implant intended for positioning in the coronary sinus by way of a jugular vein access, the tubular body 84 will have a length within the range of from about 40 cm to about 70 cm. The torque wire 86 or other control element extending through the tubular body 84 will have a corresponding length as will be appreciated by those of skill in the art.

In one embodiment, the core wire 86 comprises a nickel titanium alloy. In another embodiment, the core wire 86 comprises a cable, rod, ribbon, driver, or tube suitable for activating a shape adjustment control mechanism 90 of the implant 80. The shape adjustment mechanism 90 illustrated in FIG. 3 includes a threaded shaft 91, but may comprise other mechanisms for adjusting the shape of the implant 80, as described in greater detail below with respect to FIGS. 4-14.

The torque wire 86 may be coupled to the shape adjustment mechanism 90 at a connection 92. The connection 92 may include a permanent or detachable coupling, including a weld, a bond, an adhesive, or a mechanical coupling, such as a screw, lock, or compression fitting, as is well known to those of skill in the art. The connection 92 is strong enough to transmit force delivered from the torque wire 86 to the shape adjustment mechanism 90 to cause the implant 80 to change its shape without causing the torque wire 86 to decouple from the shape adjustment mechanism 90.

In one embodiment, the proximal end of the control line or tether 76 is coupled to an implantable housing 82. The proximal end of the tether 76 includes a proximal coupling 94, which may be similar to the distal coupling 88 described above, suitable for attachment of the tubular sheath 84 to the implantable housing 82. In the illustrated embodiment, the torque wire 86 passes through the torque sheath 84 and the proximal coupling 94, and enters the implantable housing 82 at port 96. When coupled, the torque wire 86 is free to move (e.g., rotate, move axially, etc.) with respect to the torque sheath 84 and implantable housing 82. Additional details regarding the tether 76 are provided below with respect to FIGS. 15-16.

The implantable housing 82 is generally implanted beneath the skin, near the site of entry for delivery of the implant 80 into the patient's vasculature. Additional details regarding locations of implant housing 82 implantation are provided below with respect to FIGS. 29-30. Additional details regarding embodiments of the implantable housing 82 are provided below with respect to FIGS. 20-28.

In general, the implantable housing 82 serves to protect the proximal end of the control line 54, and also may be utilized or configured to facilitate location of the proximal end of the control line 54 at some post implantation time when adjustment of the implant may be desired. At that time, the housing 82 may be exposed such as by a small incision, and opened or removed to allow access to the connector. For some configurations, the implantable housing may be accessed by a percutaneous puncture, by a rotational tool or other actuator, depending upon the design of the proximal connector 59 and/or housing 82 as will be appreciated from the disclosure herein.

Figure 4:
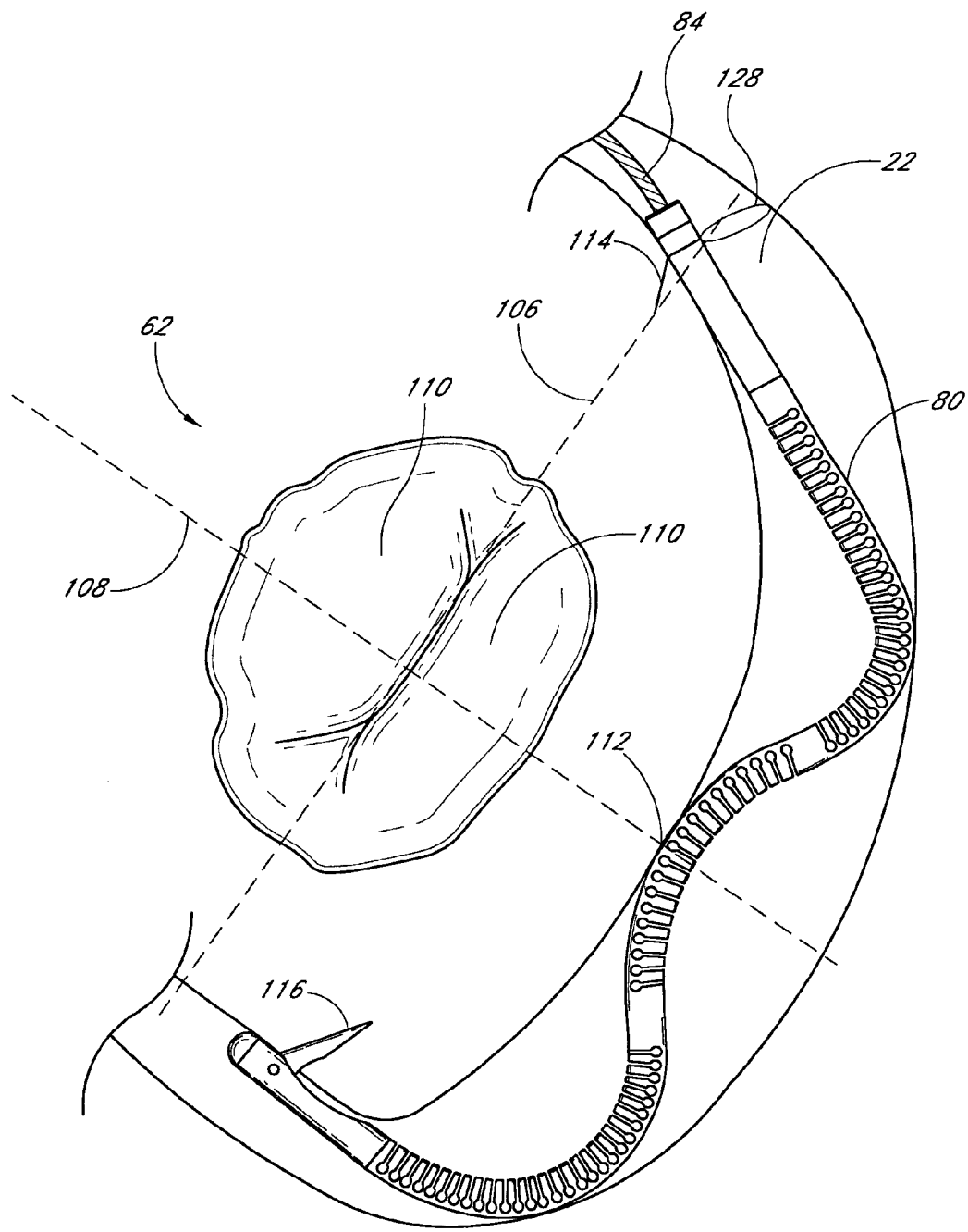
FIG. 4 is a partial cross-sectional view of the heart with one embodiment of a mitral annuloplasty device deployed within the coronary venous system.
Figure 5:
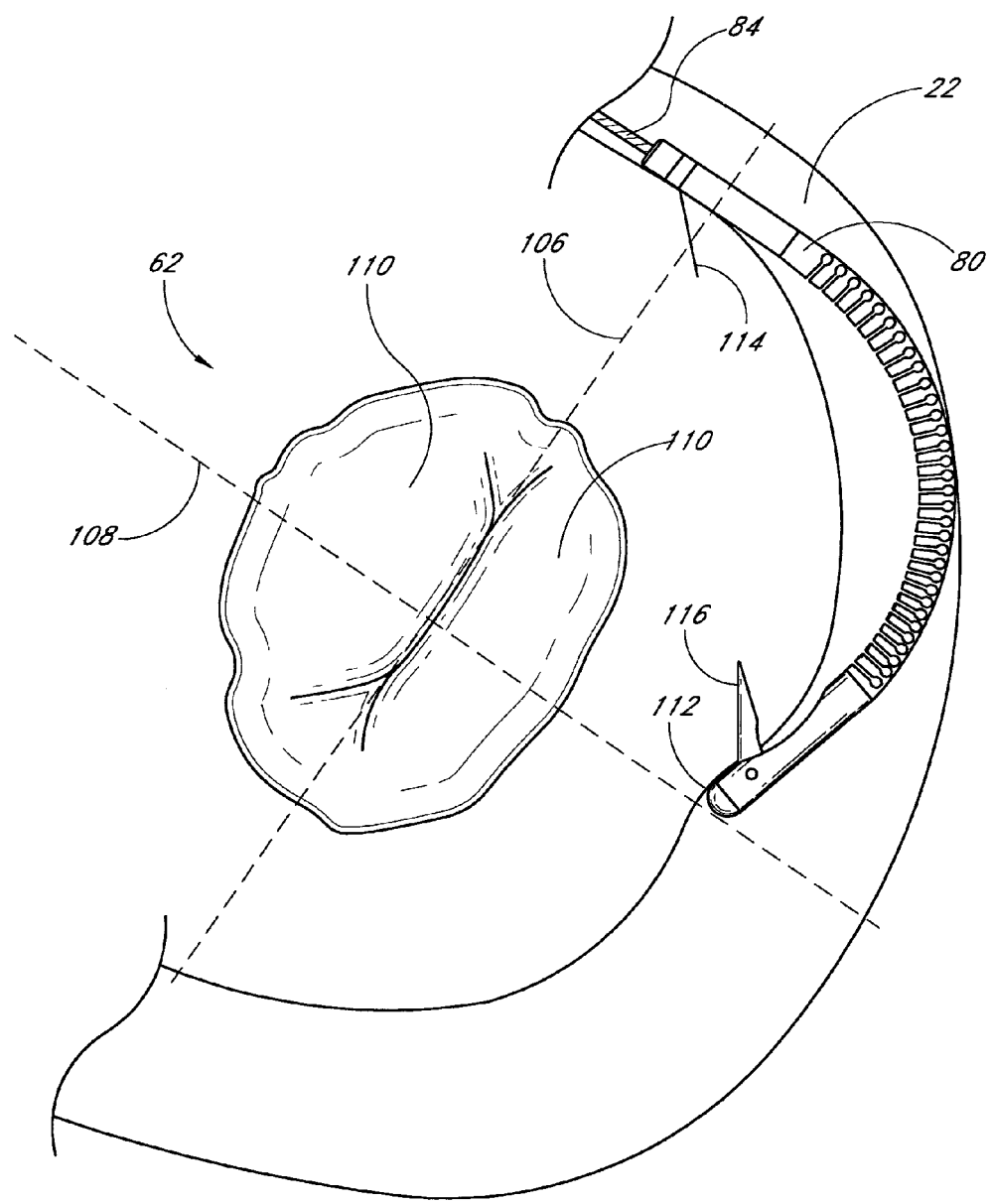
FIG. 5 is a partial cross-sectional view of the heart with another embodiment of a mitral annuloplasty device deployed within the coronary venous system.
Figure 6:
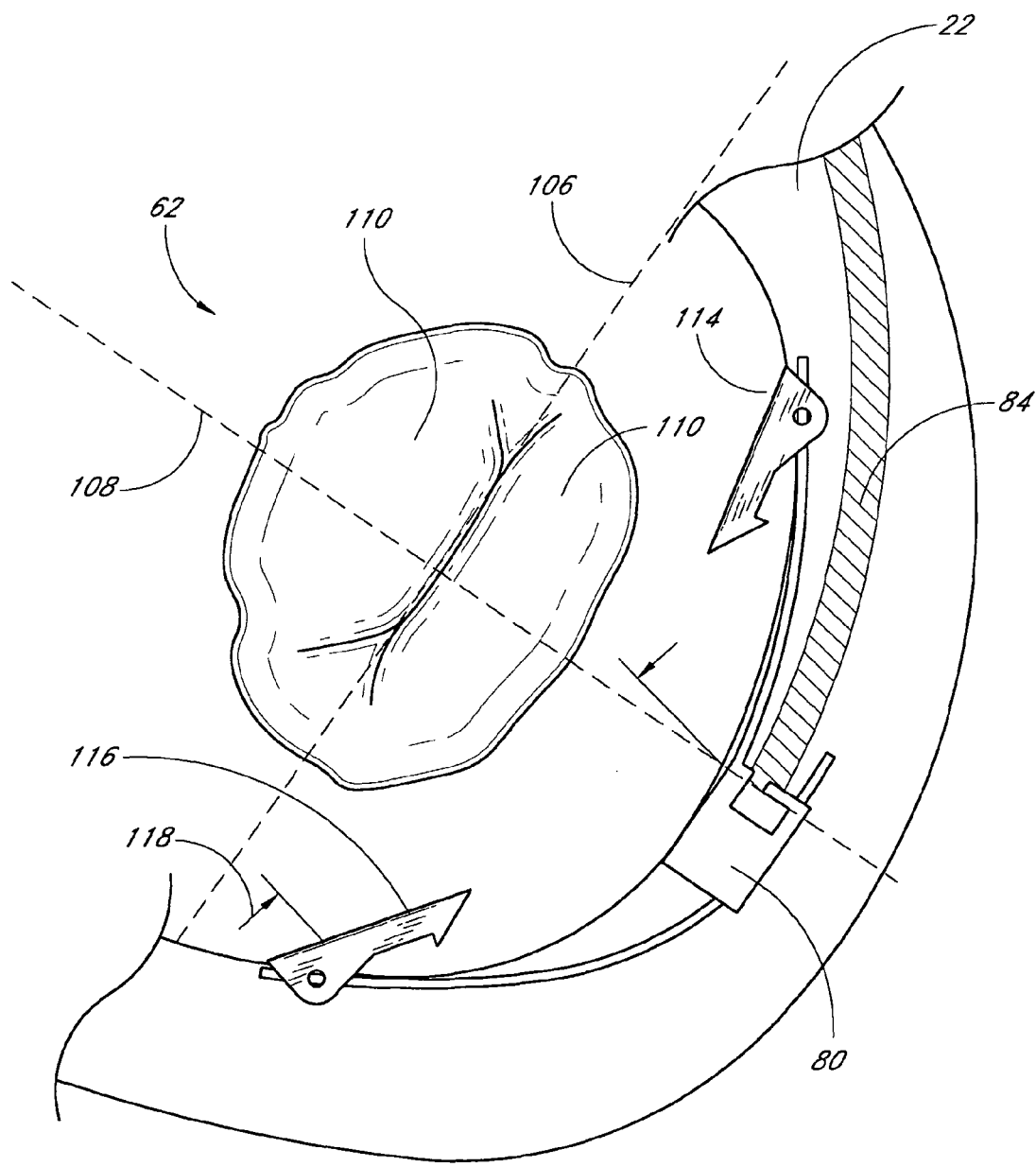
FIG. 6 is a partial cross-sectional view of the heart with another embodiment of a mitral annuloplasty device deployed within the coronary venous system.

Referring now to FIGS. 4-6, coaptive edges of opposing and adjacent leaflets of the mitral valve lie generally along a plane which is substantially parallel to the direction of blood flow through the valve, and which lies between the leaflets. A transverse coaptation axis 106 lies on the plane of coaptation. In one embodiment, a transverse pressure axis 108 is an axis which substantially bisects a leaflet 110 of the mitral valve 62, and is substantially perpendicular to the coaptation axis 106. In another embodiment, the transverse pressure axis 108 is an axis laterally offset from and parallel to an axis which substantially bisects a leaflet 110 of the mitral valve 62, and which is substantially perpendicular to the coaptation axis 106. In yet another embodiment, the transverse pressure axis 108 extends at an angle with respect to an axis which substantially bisects a leaflet 110 of the mitral valve 62 and which is substantially perpendicular to the coaptation axis 106. In such embodiment, the transverse pressure axis 108 is within the plane defined by the coaptation axis 106 and an axis which substantially bisects a leaflet 110 of the mitral valve 62.

Figure 7:
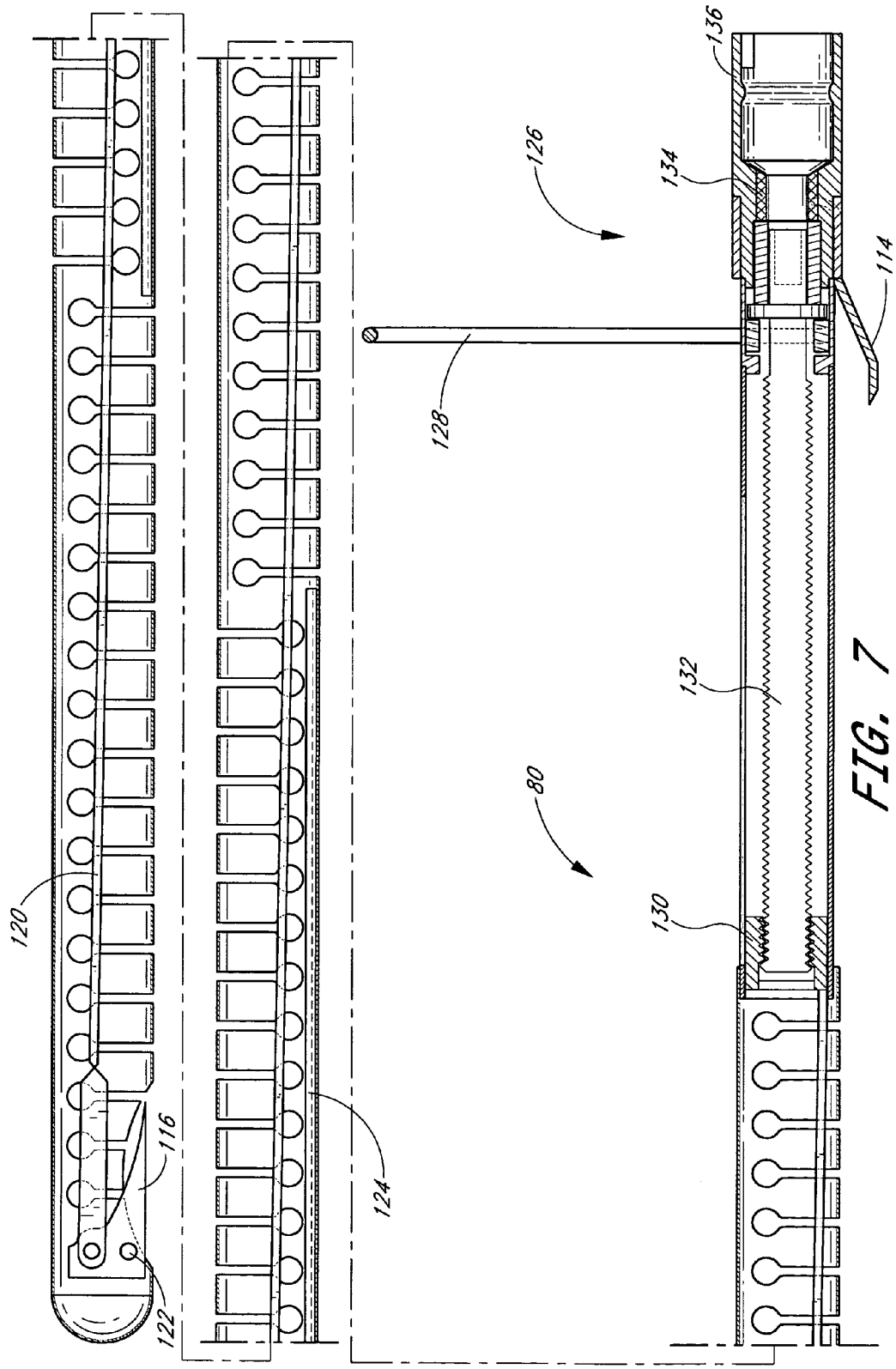
FIG. 7 shows an enlarged cross-sectional view of the mitral annuloplasty device of FIG. 4.

In one embodiment, the practitioner positions an implant or prosthesis within the coronary sinus, such as described in any of the embodiments described herein, including implant 80 and mitral annuloplasty and cardiac reinforcement device 40. The practitioner positions the implant or prosthesis with respect to a coaptation axis, or other axis, such as a transverse pressure axis. In one embodiment, as illustrated in FIG. 4 an implant 80, such as that described below with respect to FIG. 7, is designed to assume a "W" shape when deployed. The peak 112 at substantially the center of the "W" shaped implant 80 may be oriented with respect to the transverse pressure axis 108 so as to control placement of pressure upon a desired portion of the inside wall of the coronary sinus 22. The illustrated peak 112 is positioned in contact with a portion of the inside wall of the coronary sinus 22 that is substantially intersected by the transverse pressure axis 108 of the mitral valve 62. In another embodiment, the peak 112 is positioned in contact with a portion of the inside wall of the coronary sinus 22 that is an offset distance (not shown) from the intersection of the transverse pressure axis 108 of the mitral valve 62. In addition, proximal and distal anchors 114, 116 may be positioned within the coronary sinus 22 with respect to the coaptation axis 106 or transverse pressure axis 108 so as to control the placement of pressure applied to the mitral valve 62. A torque sheath 84 extends from the proximal end of the implant 80, through the patient's vasculature, to an implantable housing (not shown), as described in greater detail herein.

Figure 8:
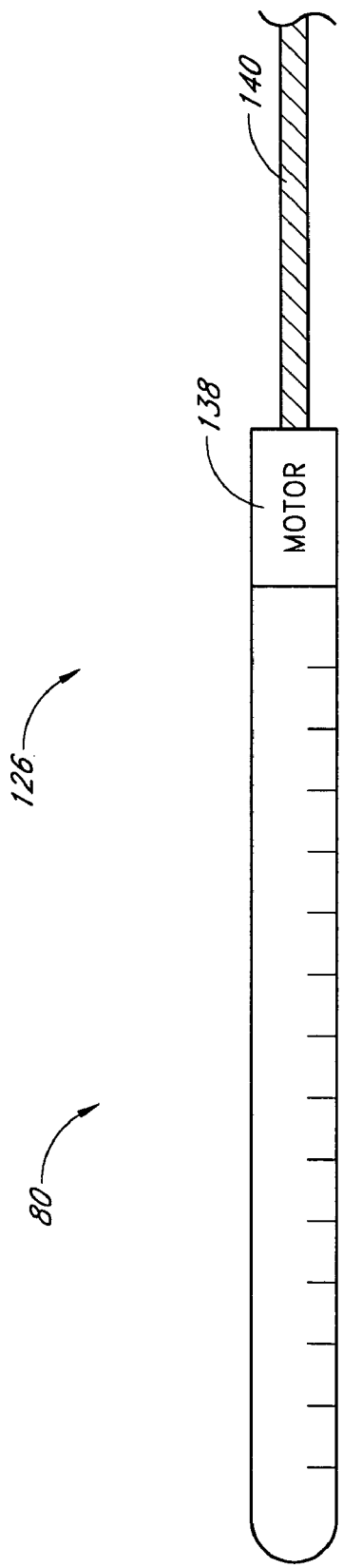
FIG. 8 shows an embodiment of the mitral annuloplasty device of FIG. 5, the device including an onboard motor.
Figure 9:
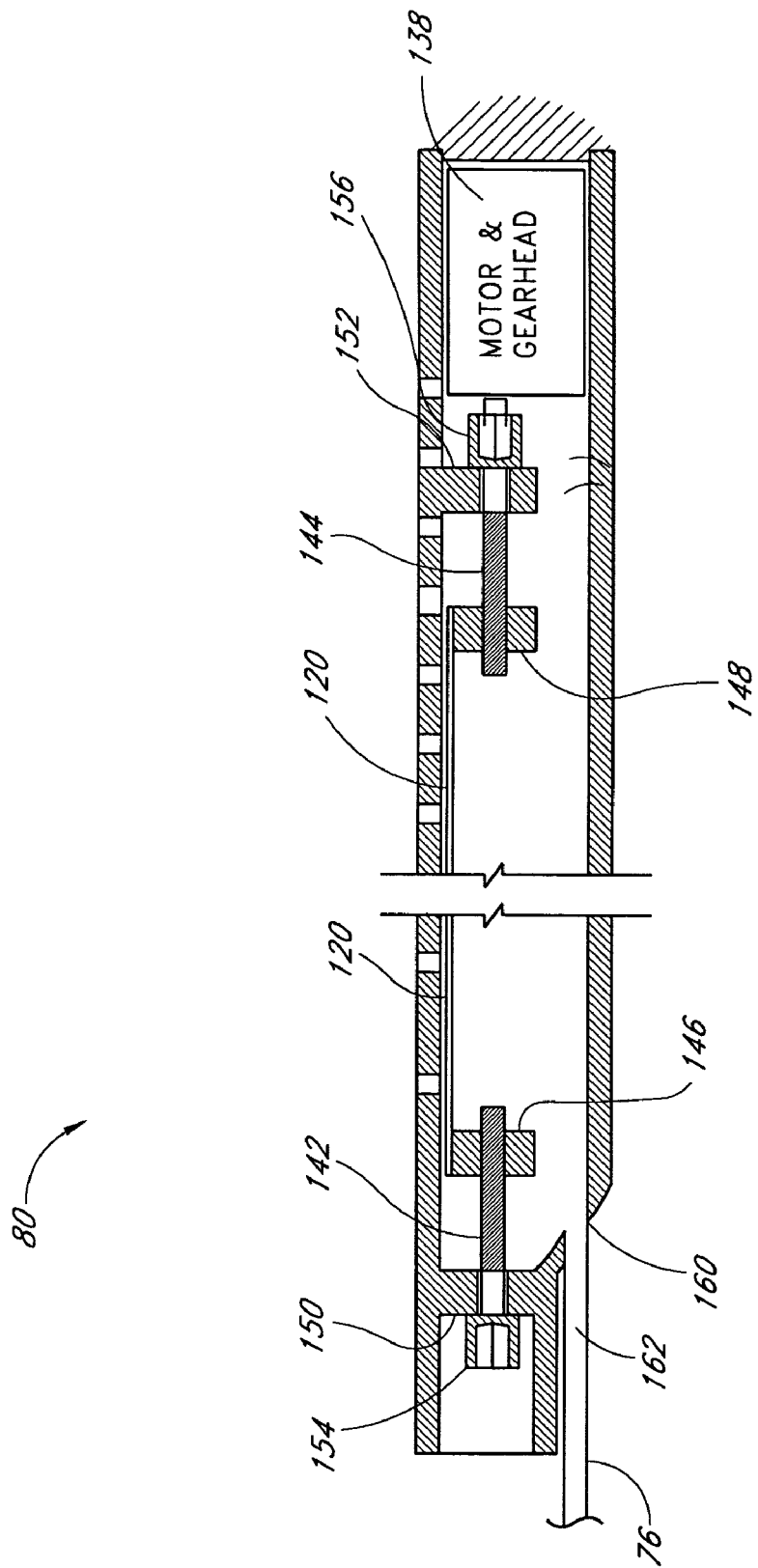
FIG. 9 shows a cross-sectional view of another embodiment of the mitral annuloplasty device of FIG. 5, the device including a distally located motor.

In another embodiment, as illustrated in FIG. 5 an implant 80, such as those described below with respect to FIG. 8-9 is designed to assume a simple curve such as a "C" shape when adjusted to the remodeling configuration. A contact surface on peak 112 at one end of the "C" shaped implant 80 is oriented with respect to the transverse pressure axis 108, so as to control placement of pressure upon a portion of the inside wall of the coronary sinus 22. As illustrated, the peak 112 is positioned in contact with a portion of the inside wall of the coronary sinus 22 that is substantially intersected by the transverse pressure axis 108 of the mitral valve 62. In another embodiment, the peak 112 may be positioned in contact with a portion of the inside wall of the coronary sinus 22 that is an offset distance (not shown) from the intersection of the transverse pressure axis 108 of the mitral valve 62. In addition, the proximal and distal anchors 114, 116 may be positioned within the coronary sinus 22 with respect to the coaptation axis 106 or transverse pressure axis 108 so as to control the placement of pressure applied to the mitral valve 62. A torque sheath 84 extends from the proximal end of the implant 80, through the patient's vasculature, to an implantable housing (not shown), as described in greater detail herein.

In another embodiment, as illustrated in FIG. 6, an implant 80, such as those described below with respect to FIGS. 10-14, is placed within the coronary sinus 22 to apply pressure to the mitral valve 62. In one embodiment, the distal anchor 116 is positioned with respect to the coaptation axis 106 or transverse pressure axis 108 so as to control the placement of pressure upon a portion of the inside wall of the coronary sinus 22. The distal anchor 116 is positioned in contact with a portion of the inside wall of the coronary sinus 22 that is an offset distance 118 from the transverse pressure axis 108 of the mitral valve 62. In another embodiment, the proximal anchor 114 of the implant 80 is positioned in contact with a portion of the inside wall of the coronary sinus 22 that is an offset distance from the coaptation axis 106 or the transverse pressure axis 108 of the mitral valve 62. A torque sheath 84 extends from the proximal end of the implant 80, through the patient's vasculature, to an implantable housing (not shown), as described in greater detail herein.

Any of a variety of implants or prostheses able to apply pressure to the heart, including any of the implants or prostheses described herein, may be provided with the remote adjustment feature in accordance with the present invention. Additional implants, such as those disclosed in U.S. application Ser. No. 10/634,655, filed Aug. 5, 2003, titled, "METHODS AND APPARATUS FOR REMODELING AN EXTRAVASCULAR TISSUE STRUCTURE," hereby incorporated by reference in its entirety, may be utilized as well. Remotely activated implants, such as those disclosed in Provisional Application Ser. No. 60/488,334, filed Jul. 18, 2003, titled, "REMOTELY ACTUATED MITRAL ANNULOPLASTY SYSTEM AND METHODS," hereby incorporated by reference in its entirety, may be utilized as well. In addition, although the embodiments described position a portion of an implant with respect to the coaptation axis 106 or transverse pressure axis 108 of the mitral valve 62, the implant portions may be positioned with respect to other axes visualized or determined upon visualization of the mitral valve 62 leaflets 110 or other anatomical landmark, or optimized by real time hemodynamic feedback. Devices and methods for visualizing or determining the orientation of the mitral valve leaflets are disclosed in U.S. application Ser. No. 10/688,712, filed Oct. 17, 2003, titled "HEART VALVE LEAFLET LOCATOR" which is hereby incorporated by reference in its entirety.

Referring to FIG. 7, there is illustrated an enlarged side elevational schematic view of the implant 80 illustrated in FIG. 4. The distal anchor 116 may be deployed by axial proximal tension on a pull wire 120. The pull wire 120 is pivotally connected to the distal anchor 116, at a position which is offset laterally from an axis of rotation. The axis of rotation is concentric with one or more pins 122 which pivotally retain the distal anchor 116 in position at the distal end of the implant 80. In the illustrated embodiment, proximal axial advancement of the pull wire 120 will cause the distal anchor 116 to incline radially outwardly with respect to the longitudinal axis of the implant 80.

An optional spine support 124 is illustrated at the central segment of the implant 80. The spine support 124 may comprise any of a variety of elements, such as a flexible ribbon of stainless steel, nitinol or other material, for enhancing the column strength of the implant 80 in this or other desired region.

In one embodiment, the proximal end 126 of the implant 80 includes a lateral displacement hoop 128. Displacement hoop 128 may comprise any of a variety of structures, such as a loop or other resilient element which may be biased radially outwardly from the longitudinal axis of the implant 80 to contact the adjacent side of the vessel wall and bias the proximal anchor hook 114 in the direction of, in the case of the illustrated design, the mitral valve side of the vessel wall.

In one embodiment, the proximal end 126 of the implant 80 also includes a sliding nut 130 which is coupled to the proximal end of the pull wire 120. As a threaded screw 132 is rotated with respect to the implant 80, the nut 130 moves in the proximal direction, thereby increasing tension on the pull wire 120. As tension is applied to the pull wire 120, the distal anchor 116 is deployed, and the shape of the implant 80 is changed from a substantially straight, flexible shape, to a substantially rigid, deployment shape.

In one embodiment, the deployment shape is the shape of the letter "W," such as illustrated in FIG. 4. In other embodiments, the deployment shape is the shape of the letter "C," such as illustrated in FIGS. 5 and 6, and described in greater detail below. Other shapes may be utilized as is well known to those of skill in the art.

The proximal end 126 of the implant 80 also includes a torque sheath coupling 134. The torque sheath coupling 134 couples the torque sheath 84 (not shown) to the implant 80. In one embodiment, the torque sheath coupling 134 is an adhesive, such as an epoxy, to provide a permanent bond. In other embodiments, the torque sheath coupling 134 is a laser weld, or a releasable connection such as a threaded or bayonet mount. A wide variety of structures may be employed as the torque sheath coupling 134, as will be understood by those of skill in the art. The torque sheath coupling 134 generally does not allow the torque sheath 84 to rotate with respect to the implant 80.

The torque wire 86 (not shown) travels through the torque sheath 84 and is rotationallly coupled to the proximal end of the threaded screw 132. Rotation of the torque wire 86 with respect to the torque sheath 84 causes the threaded screw 132 to rotate with respect to the implant 80, thereby causing the nut 130 to move axially along the threaded screw 132. Such movement of the nut 130 causes the implant 80 to change its shape, as described in greater detail above.

The proximal end 126 of the implant 80 also includes a catheter coupling 136. The catheter coupling 136 releasably couples a delivery catheter (not shown) to the implant 80. Additional discussion regarding the method of delivery of the implant 80 to the coronary sinus 22 of the medial patient is described in greater detail below with respect to FIGS. 29-30.

In any of the embodiments disclosed herein, in which a tubular body is provided, the space within the tubular body may be utilized to carry any of a wide variety of drug delivery vehicles. For example, microporous beads, filaments or other structures may be carried within the tubular body. Any of a variety of dissolvable or absorbable gels or other carriers may be utilized, for carrying one or more active agents, for delivery from the implant into the vessel or vessel wall. The active agent may be released from the carrier using any of a variety of known drug delivery techniques, such as by erosion of the carrier, migration of the active agent through a microporous structure, or other as is known in the drug delivery arts.

The active agent carrier carried within the implant may be provided with any of a variety of active agents. These agents include anticoagulants, anti-inflammatory agents, drugs to inhibit smooth muscle cell proliferation or other responses to injury, antibiotics, drugs to enhance endothelial growth, or others known in the art.

Another embodiment of implant 80 is shown in FIG. 8. Implant 80 is similar to implant 80 of FIGS. 4, 5, and 7, except that implant 80 of FIG. 8 includes a motor 138 coupled to the implant 80 proximal end 126. The motor 138 is coupled to the threaded screw 132 (not shown) inside of the implant, and causes the implant 80 to change its shape by rotating the threaded screw 132 as described in greater detail above. The motor 138 may include a gearhead (not shown) suitable for providing adequate torque to the threaded screw 132, as is well known to those of skill in the art.

At least one lead 140 is coupled to the motor 138. The lead 140 travels through a tubular sheath 84 (not shown), and terminates inside of an implantable housing 82 (not shown), as described in greater detail herein. Electrical signals coupled to the lead 140 cause the motor to turn in either the clockwise or counterclockwise directions, thereby affecting the implant 80 shape. In one embodiment the lead 140 includes a single conductor (not shown), although in other embodiments, the lead 140 includes two, three, or more than three conductors. Each conductor is able to conduct electrical signals from the housing 82 to the implant 80, and is electrically insulated so as not to affect or be affected by the other conductors or parts of the implant 80.

Referring now to FIG. 9, there is provided an implant 80 including a motor and gearhead 138, pull wire 120, proximal and distal threaded shafts 142, 144, proximal and distal nuts 146, 148, proximal and distal blocks 150, 152, and proximal and distal couplings 154, 156. In one embodiment, the implant 80 is sealingly attached to a tether 76 at interface 160 by welding, adhesive bonding, or other mechanism, as is well known to those of skill in the art. At least one wire 162 preferably connects to the motor and gearhead 138, and preferably is routed through the implant 80 and tether 76, and to the remote implantable housing 82 (not shown), as described in greater detail herein.

The configuration or shape of the implant 80 can be adjusted in at least two different ways. Manual adjustment can be achieved by turning proximal threaded shaft 142 so as to draw proximal nut 146 towards proximal block 150 in a manner similar to that described above with reference to FIG. 7. Electrical adjustment can be achieved by turning distal threaded shaft 144 so as to draw distal nut 148 towards distal block 152. Motor and gearhead 138 is rotationally coupled to distal threaded shaft 144 so as to provide rotation of distal threaded shaft 144 in response to signals carried by the at least one wire 162. In both cases, pull wire 120 is tensioned to affect a change in implant 80 shape, as described above.

In the embodiment of FIG. 9, the mechanical coupling and associated control components on the proximal end of the device may be deleted, leaving only motor and gearhead 138 as the driving mechanism. In that construction, the motor and gearhead would be responsible for both primary tensioning of the implant upon initial implantation, as well as subsequent post implantation adjustment. In the embodiment as illustrated, however, the primary adjustment upon implantation may be accomplished by a rotatable core contained by the deployment catheter, for manipulating the proximal threaded shaft 142. The deployment catheter may thereafter be decoupled from the implant, leaving only the electrical conductor such as wire 162 trailing transluminally or otherwise extending to the percutaneous access site. The use of motor and gearhead 138 for post implantation adjustment conveniently eliminates the need for recoupling a mechanical adjustment catheter to the implant 80, which may be complex in a beating heart environment.

There is provided in FIGS. 10-12 a partially cross-sectioned side elevational view of an alternate construction of an implant 80, similar to that illustrated in FIG. 6, above. The implant 80 includes a proximal section 164, a distal section 166, and a tensioning element 168. The tensioning element 168 couples the proximal section 164 to the distal section 166, and is used to apply and release tension therebetween.

As illustrated in FIG. 10, the proximal section 164 includes a proximal tissue anchor 114, and a proximal ribbon 170. The proximal tissue anchor 114 may be laser cut from stainless steel tube, and has an arcuate cross-sectional shape (not shown). Alternatively, any of a variety of tissue anchor designs and materials may be employed, as described herein, and as are known to those of skill in the art. In one embodiment, the proximal tissue anchor 114 includes a penetrating point 172, and two barbs 174 to hold the proximal tissue anchor 114 securely in place once deployed. A variety of penetrating points 172 and barbs 174 may be used to achieve desired clinical results, and the particular proximal tissue anchor 114 design may vary depending upon the particular clinical requirements.

In one embodiment, the proximal tissue anchor 114 includes two holes 176 that are used to rotatably couple the proximal tissue anchor 114 throughout a limited range of rotation with a pivot 178 that is coupled to the proximal ribbon 170. One embodiment of such pivot 178 is shown in greater detail on FIG. 12. The pivot 178 may be integral to the material of the proximal ribbon 170, or may include a pin, or other device coupled to the proximal ribbon 170. The proximal section 164 also includes a spring 180, used to bias the proximal tissue anchor 114 so that its penetrating point 172 rotates away from the proximal ribbon 170 and towards tissue when deployed. In one embodiment, the spring 180 is cut from the same tubing used to form the proximal tissue anchor 114, and is integral thereto. In another embodiment, the spring 180 has a torsional design, as is well known to those of skill in the art.

The overall length of the proximal tissue anchor 114 preferably is about 6 mm, although the actual length will be selected based upon the particular requirements of the clinical setting. In one embodiment, the length of the proximal tissue anchor 114 will be selected such that it does not penetrate all the way through the wall of the coronary sinus when deployed. In general, the length of the proximal tissue anchor 114 is in the range between about 1 mm and about 15 mm.

Distal section 166 preferably includes a distal tissue anchor 116, a distal ribbon 182, and a spring 180, as shown in FIG. 10. Distal tissue anchor 116 is similar to proximal tissue anchor 114, and has similar characteristics and dimensions as described in greater detail above. In one embodiment, distal ribbon 182 includes multiple slots 184 to interface with the tensioning element 168, as described in greater detail below. The slot 184 pitch, or center-to-center spacing of the slots 184, partially defines the resolution of the adjustability of the tension applicable between the proximal and distal tissue anchors 114, 116. In one embodiment, the slot pitch is about 1 mm. Alternatively, the slot pitch is between 0.1 mm and 3 mm. In another embodiment, the slot pitch is not constant along the length of the distal ribbon 182. The distal ribbon 182 may be designed to have a greater pitch, or slot width towards the proximal end of the distal ribbon 182, and a smaller pitch or slot width towards the distal end of the distal ribbon 182. Alternatively, the distal ribbon 182 may have no slots such that continuous instead of stepped movement of the distal ribbon 182 is used to apply tension between the proximal and distal tissue anchors 114, 116. The method of applying tension between the proximal and distal tissue anchors 114, 116 is described in greater detail below. The distal ribbon 182 extends through the lumen of a torque sheath 84 (not shown), and terminates in an implantable housing 82, such as described in greater detail herein.

As shown in FIGS. 10 and 11, the implant 80 also includes a tensioning element 168. In one embodiment, the tensioning element 168 includes a housing 188, latch 190, spacer 192, and insert 194. In one embodiment, the housing 188 is made from a section of stainless steel tubing, although housings 188 of other shapes and materials may be used. In one embodiment, the housing 188 is made from nickel titanium tubing. The proximal ribbon 170 preferably is attached to the inside lumen of the housing 188 using any of a variety of methods, including welding, bonding, or by using any of a variety of fasteners, as is well known to those of skill in the art. In one embodiment, the proximal ribbon 170 is attached to the housing 188 such that the axial position of the proximal tissue anchor 114 is fixed with respect to the housing 188.

The housing 188 also includes a latch 190 that preferably is attached to a spacer 192 at the latch's 190 distal end. The latch 190 includes a tang 196 that bends towards the distal ribbon 182 at an angle relative to the distal ribbon 182. The tang 196 is designed to travel through an opening 198 in the spacer 192, and engage a slot 184 in the distal ribbon 182. By engaging the slot 184 in the distal ribbon 182, the latch 190 prevents axial movement of the distal ribbon 182, and distal tissue anchor 116, in the distal direction. The opening 198 in the spacer 192 is of sufficient dimension to allow the tang 196 of the latch 190 to flex enough to disengage the slot 184 in the distal ribbon 182 when the distal ribbon 182 is moved in the proximal direction. The interface between the latch 190 of the tensioning element 168 and the slot 184 of the distal ribbon 182 functions as a ratcheting mechanism. The ratcheting mechanism allows stepped movement of the distal ribbon 182 as it is moved in the proximal direction (as described in greater detail below), yet prevents the distal ribbon 182 from moving in the distal direction. The amount of movement of each ratcheting step is related to the pitch between the distal ribbon 182 slots 184, as described above.

In another embodiment, the distal ribbon 182 does not contain slots. In such embodiment, friction between the tang 196 of the latch 190 and the distal ribbon 182 is sufficient to allow continuous, e.g., non-stepped, or infinitely adjustable, movement of the distal ribbon 182 in the proximal direction, yet prevent movement of the distal ribbon 182 in the distal direction. In another embodiment, shallow depressions, ribs or other texture, or partial thickness slots are added to the surface of distal ribbon 182 to provide enhanced friction against tang 196. In one embodiment, movement of the distal ribbon 182 in the proximal direction may be achieved by releasing, or disengaging the tang 196 of the latch 190 from the distal ribbon 182.

The housing 188 may also include a latch release ribbon 200 that in one embodiment is disposed between the spacer 192 and the distal ribbon 182, as illustrated in FIG. 10. The latch release ribbon 200 is also axially moveable with respect to the housing 188 and the distal ribbon 182. In the illustrated embodiment, as the latch release ribbon 200 is moved proximally, the tang 196 of the latch 190 is lifted such that it disengages the slot 184 of the distal ribbon 182. While disengaged from the latch 190, the distal ribbon 182 may be moved in the distal direction, thereby increasing the distance between the proximal and distal anchors 114, 116.

A tubular sheath 84 is attached to the implant 80 such as on the proximal side of the tensioning element 168. The latch release ribbon 200 and distal ribbon 182 extend axially within a lumen of the sheath 84 from the implant 80 to a proximal implantable housing (not shown). Access to the latch release ribbon 200 and distal ribbon 182 from the implantable housing allows for remote adjustment of the implant 80 shape.

Portions of the lumen of the housing 188 may be filled with an insert 194, as illustrated in FIG. 11. As shown, insert 194 fills the spaces between the spacer 192 and the housing 188 of the tensioning element 168. In one embodiment, the portion of the lumen between the distal ribbon 182 and the housing 188 does not contain an insert 194, although in other embodiments it does. It may be advantageous to omit an insert 194 between the distal ribbon 182 and the housing 188 so as to reduce friction on the distal ribbon 182 when moving the distal ribbon 182 with respect to the housing 188.

FIG. 12 illustrates one embodiment of the distal ribbon 182, as described in greater detail above. The illustrated distal ribbon 182 is about 65 cm long, although the length of the distal ribbon 182 may be selected for the clinical requirements of the particular treatment. In general, the length of the working zone of the distal ribbon 182 (e.g., the zone containing slots 184) is in the range between about 2 cm and about 20 cm. The length of the proximal ribbon 170 has similar dimensions, such that the overall length of the implant 80 is in the range between about 2 cm and about 20 cm, often in the range between about 5 cm and about 15 cm, and in many implementations in the range between about 7 cm and about 10 cm. In one embodiment, the overall length of the implant 80, excluding the control line, is about 9 cm.

In the illustrated construction, the crossing profile of the implant 80 is determined by the diameter of the housing 188, as illustrated in FIG. 11. In one embodiment, the diameter of the housing 188 is selected so that the implant 80 may be delivered inside of a catheter having an lumen with a diameter in the range between 6 French (approximately 0.079 inches) and 20 French (approximately 0.262 inches). In one embodiment, the length of the housing 188, as shown in FIG. 10 is in the range between about 3 mm and about 10 mm, preferably in the range between about 5 mm and about 8 mm, and more preferably in the range between about 6 mm and about 7 mm.

Additional details and variations regarding the implant 80 are disclosed in U.S. patent application Ser. No. 10/688,712, filed Oct. 17, 2003, titled, "HEART VALVE LEAFLET LOCATOR," and U.S. application Ser. No. 10/634,655, filed Aug. 5, 2003, titled, "METHODS AND APPARATUS FOR REMODELING AN EXTRAVASCULAR TISSUE STRUCTURE," which are incorporated by reference in their entireties herein.

Figure 14:
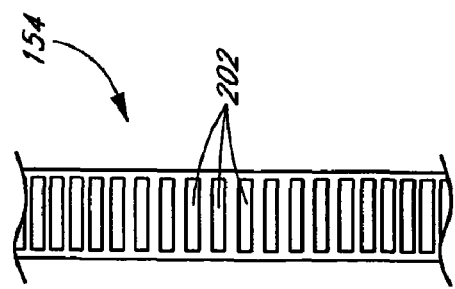
FIG. 14 shows a detailed view of FIG. 13 taken along the line 14-14.
Figure 13A:
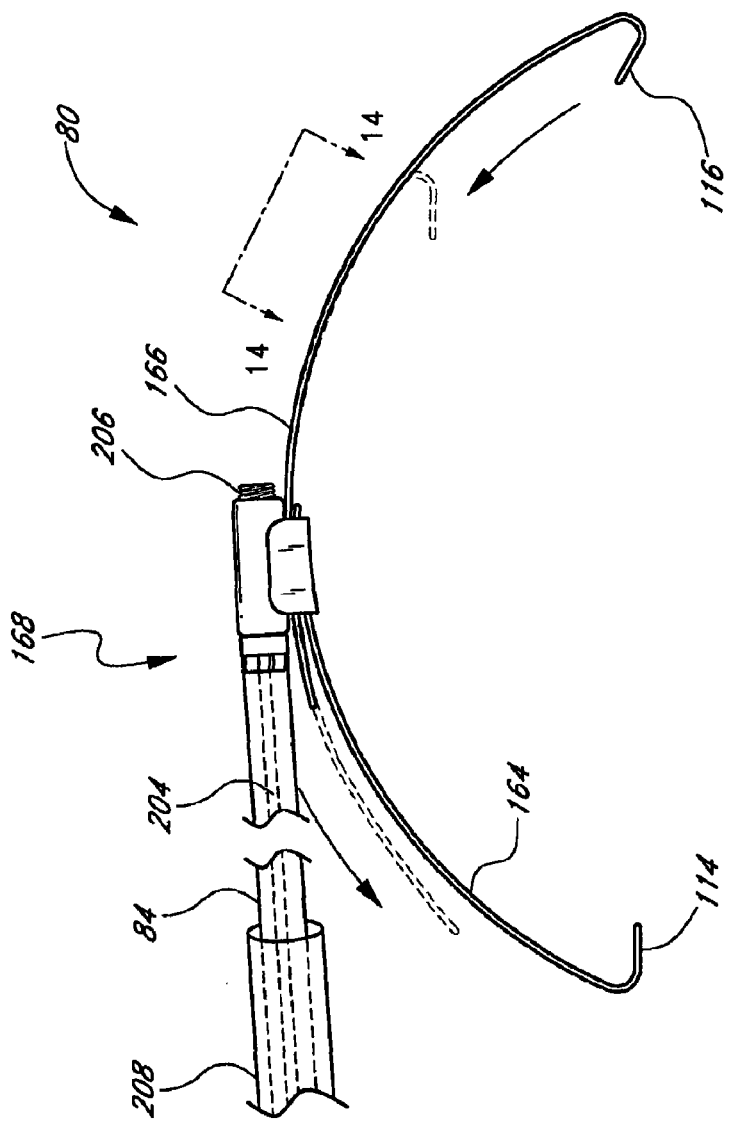
FIG. 13A shows an alternative embodiment of the mitral annuloplasty device of FIG. 6 coupled to a deployment catheter.

A further implementation of the invention may be understood by reference to FIGS. 13A-14. In this construction, a distal section 166 has one or more tissue anchors 116, and a proximal section 164 has one or more proximal tissue anchors 114. The distal tissue anchor 116 and/or the proximal tissue anchors 114 may either be passive (as illustrated) or active, such that the anchors are pivotably or angularly adjustably carried by the implant. Active tissue anchors may either incline in response to positioning or tightening of the device, or be controlled by a separate rotatable or axially moveable control element. The proximal tissue anchors 114 and distal tissue anchors 116 need not both be active or passive. For example, the distal tissue anchor 116 may be actively engageable with the adjacent tissue such as by manipulation of a tissue engagement control. The proximal tissue anchor 114 may be passively engageable with the adjacent tissue. The reverse may also be accomplished, where the distal tissue anchor 116 is passively engageable with adjacent tissue and the proximal tissue anchor 114 is controllably engageable utilizing a control on the deployment catheter. The foregoing discussion concerning the active or passive tissue anchors applies to all of the embodiments herein, as will be apparent to those of skill in the art in view of the disclosure herein.

A tensioning element 168 is provided at about a junction between the distal segment 166 and the proximal segment 164. The tensioning element 168 is adapted to apply tension between the proximal anchors 114 and the distal anchors 116.

In one construction, at least one of the proximal section 164 and distal section 166 comprises a plurality of transverse engagement structures such as slots 202, as shown in FIG. 14. The tensioning element 168 includes a rotatable threaded shaft 206 oriented such that the threads engage the transverse slots 202 on the proximal or distal section 164, 166. Rotation of the threaded shaft using any of a variety of rotatable engagement configurations disclosed elsewhere herein will cause axial movement of the corresponding proximal or distal section 164, 166, as will be understood by those of skill in the art.

In one particular embodiment, the proximal section 164 is secured to the tensioning element 168. The distal section 166 is axially moveably engaged with the tensioning element 168 by engagement of one or more rotatable threads within the tensioning element 168, in a plurality of transverse slots on the distal section 166. Rotation of a rotatable driver 204 in a first direction will draw the distal anchor 116 in a proximal direction, thereby decreasing the distance between the proximal anchor 114 and the distal anchor 116. Alternatively, the distal section 166 may be fixed with respect to the tensioning element 168, and the proximal section 164 may be axially advanced or retracted based upon the rotation of a rotatable driver 204. In a further alternative, each of the proximal section 164 and the distal section 166 may engage a threaded shaft 206 in the tensioning element 168, to enable the axial distance between the proximal anchor 114 and the distal anchor 116 to be adjusted.

The torque sheath 84, rotatable driver 204, and implant 80 are delivered to the target location within the patient's vasculature by a catheter 208. In one embodiment the rotatable driver 204 comprises a torque wire 86, as described in greater detail herein. The rotatable driver 204 travels through a torque sheath 84, which is fixed to the tensioning element 168. Rotation of the rotatable driver 204 with respect to the torque sheath 84 causes rotation of the threaded shaft 206 with respect to the tensioning element 168. The proximal end of the torque sheath 84 and rotatable driver 204 (or torque wire 86) extend to a remote implantable housing (not shown) so that remote adjustment to the implant 80 may be made as described in greater detail elsewhere herein.

Each of the proximal anchors 114 and distal anchors 116 may be either actively deployed such as has been described previously herein, or may be fixed with respect to their corresponding section 164, 166. In an embodiment in which the anchor is fixed with respect to its corresponding support section, the anchors are retracted within a deployment sleeve such as catheter 208 for transluminal navigation. The deployment sleeve is advanced distally through the coronary sinus to the distal point of attachment of distal anchor 116. Proximal retraction of the outer sleeve with respect to the implant will release the distal anchor 116, which may incline radially outwardly in the proximal direction due to its own internal bias. Proximal traction on the distal anchor 116 will cause the distal anchor to engage tissue at the distal attachment site. The outer tubular sleeve may be further proximally retracted to release the proximal anchor 114. Rotation of the rotatable driver following engagement of the anchors will apply compressive force to the mitral valve annulus. Any of a variety of lateral engagement structures, may be adapted for use with the present embodiment, to focus pressure on a specific anatomical site such as the posterior leaflet of the mitral valve.

Figure 13B:
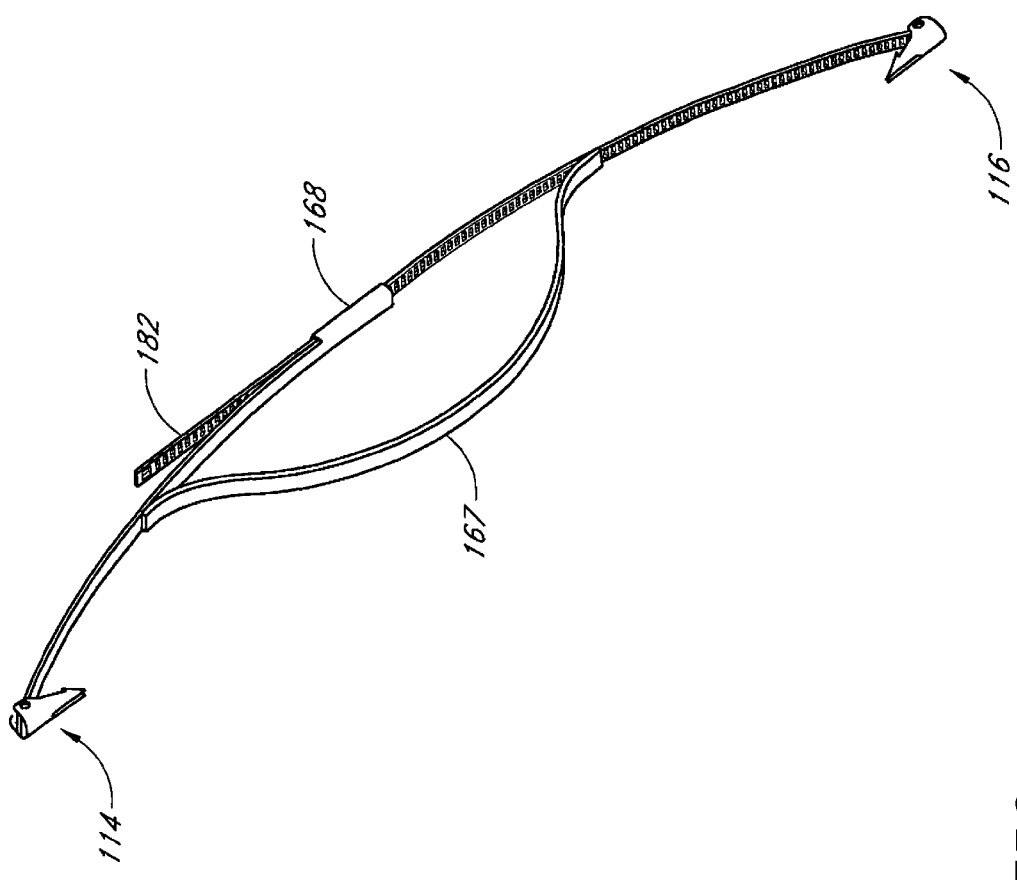
FIG. 13B shows a variation of the implant of FIG. 13A having a lateral compression element.

In another embodiment, a compression element 167 may be formed from an elongate flexible ribbon extending along the concave side of at least one of the distal section 166 and proximal section 164. A proximal end of the compression element may be secured with respect to the proximal section 164, and a distal end of the compression element may be secured with respect to the distal section 166. Upon manipulation of the tensioning element 168 to reduce the axial length of the implant 80, the compression element will extend radially inwardly from the concave side of the device. See, e.g., FIG. 13B, illustrating a lateral compression element 167 which can be provided on either the FIG. 10 or the FIG. 13A constructions.

In the foregoing embodiment, deployment of the compression element 167 is responsive to shortening or tensioning of the device. In an alternate implementation of the invention, the lateral advance of the compression element may be controlled independently of tensioning the tensioning element 168. In this embodiment, the tensioning element 168 may be adjusted to seat the proximal anchors 114 and distal anchors 116, and to apply a degree of tension on the mitral valve annulus. During or following the tensioning step, the compression element may be laterally deployed. Lateral deployment may be accomplished by rotating a rotatable driver or axially moving an axial driver within the deployment catheter, inflating a laterally expandable balloon by way of an inflation lumen in the deployment catheter, or through any of a variety of structures which will become apparent to those of skill in the art in view of the disclosure herein.

Referring now to FIG. 15, there is shown a fragmentary view of a deployment catheter 208 and tether 76 in accordance with one embodiment of the present invention. The tether 76 is carried at least partially within a tether lumen 214 (shown in FIG. 16) of the deployment catheter 208, and couples an implant (not shown) to an implantable proximal connector (not shown). The tether 76 includes a torque sheath 84 and a torque wire 86 as described in greater detail above. In one embodiment, the torque wire 86 is a cable or a ribbon, as described above. The distal end of the torque wire 86 is coupled to a driver 210, such as any of the drivers described herein that are used to adjust the shape of an implant. The distal end of the torque sheath 84 is configured to couple to the torque sheath coupling 134 on the implant, described with respect to FIG. 7 above. In one embodiment, the tether 76 includes a guidewire lumen (not shown).

The proximal end of the tether 76 includes a housing coupling 212, which is adapted to connect the torque sheath 84 to an implantable housing which carries the proximal connector. The diameter of the torque sheath 84 and the housing coupling 212 is small enough to fit inside of the tether lumen 214 of the deployment catheter 208. As will be described in greater detail below, once the deployment catheter 208 delivers the implant to the target location within the patients vasculature (e.g., the coronary sinus), the deployment catheter 208 is decoupled from the implant, while the torque sheath 84 and torque wire 86 remained coupled to the implant. At deployment of the implant, the proximal ends of the deployment catheter 208, the torque sheath 84, and torque wire 86 are external to the patient's vasculature, and accessible to the physician to affect the implant's shape. As described above, rotation of the torque wire 86 with respect to the torque sheath 84 will affect the shape of the implant. The deployment catheter 208 is removed from the patient by withdrawing it over the proximal end of the torque sheath 84 and torque wire 86. Once the deployment catheter 208 is removed, the torque sheath 84 is capped or attached to an implantable housing, and the torque wire 86 is placed inside of the implantable housing for future access by the physician. Additional details regarding the implantable housing are provided below.

Figure 17:
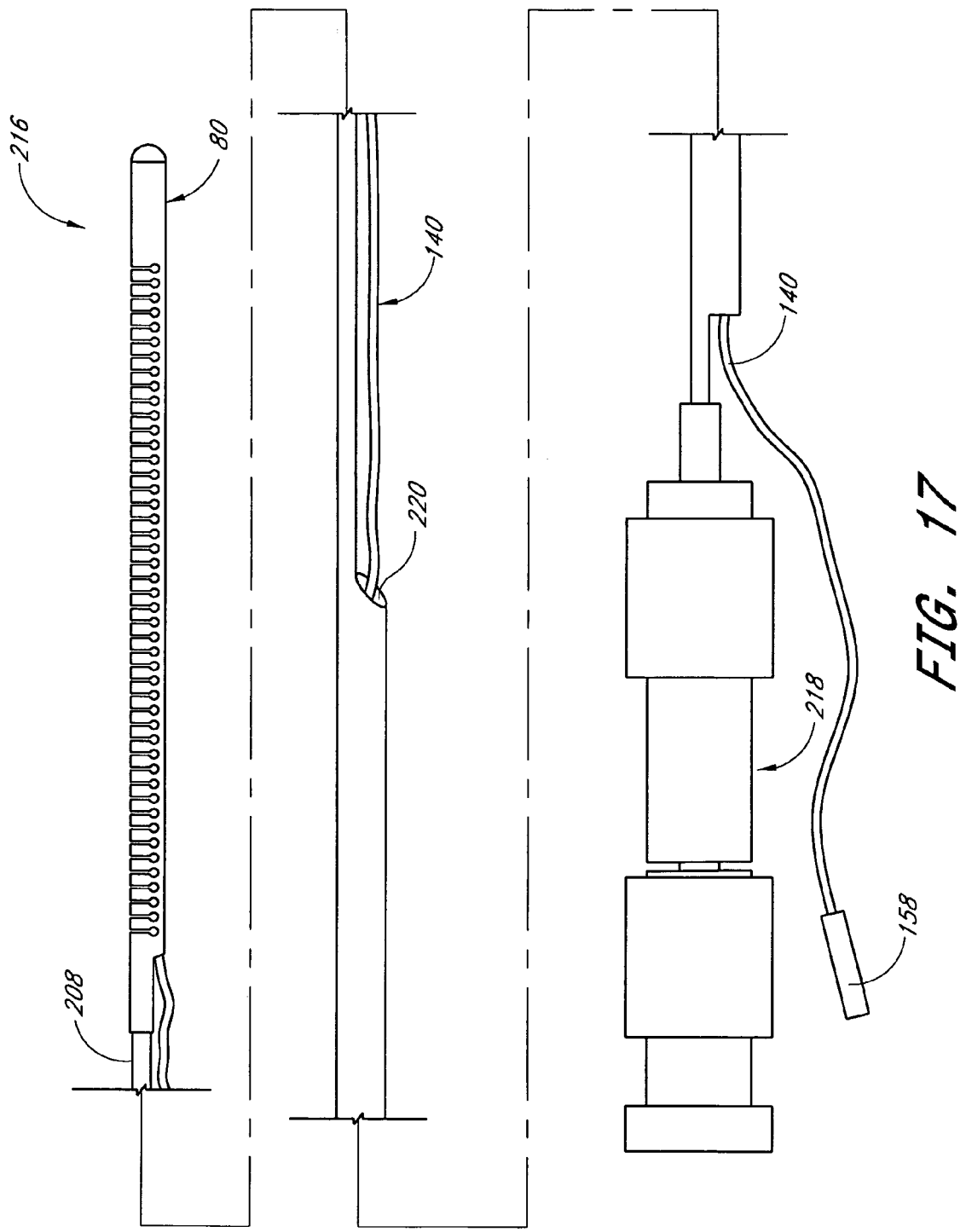
FIG. 17 shows a side elevational view of a deployment catheter suitable, for example, for delivering the mitral annuloplasty device of FIGS. 8 and 9.

Referring to FIG. 17, one embodiment of an implant deployment system 216 delivery catheter 208 suitable to deliver the implant 80 of FIGS. 8 and 9 is provided. Delivery catheter 208 is coupled to a handle 218 at the delivery catheter 208 proximal end. The handle 218 includes controls for adjusting and deploying the implant. In one embodiment, the implant 80 is releasably coupled to the delivery catheter 208 distal end. The implant 80 may be deployed by withdrawing delivery catheter 208 while stabilizing the position of the implant 80 with a pushwire or outer sheath (not shown). A lead 140 travels through a lead lumen 220, and terminates in a connector 158.

FIG. 18 is an enlarged view of a driver or torque wire 86 apart from the torque sheath 84 and other components of the implant deployment system. The torque wire 86 includes an elongate shaft and extends from a proximal end 222 to a distal end 224. The torque wire 86 may be constructed from a nickel titanium (NiTi) alloy, however, other suitable materials may also be used. The proximal end 222 of the torque wire 86 is desirably coupled for rotation with respect to an implantable housing (not shown), which will be described in greater detail below. The distal end 224 is preferably non circular such as hex-shaped in cross-section and is sized to engage the corresponding hex-shaped cavity of an element on the implant such as a threaded screw, as is described above with respect to FIGS. 4, 5, 7, and 13. Rotation of the torque wire 86 results in corresponding rotation of the threaded screw, and subsequent adjustment of the implant's shape. Other suitable arrangements to permit rotational coupling of the torque wire 86 and threaded screw may also be used, such as using complementary polygonal or other non-round cross-sectional shapes for the mating components.

The torque wire 86 may include a shoulder 226 disposed on a proximal side of the hex-shaped distal end 226. Preferably, the diameter of the shoulder 226 is larger than a width W of the hex-shaped distal end 224, as shown in FIG. 19. In one preferred embodiment, the diameter of the shoulder 226 is approximately 0.032"-0.040" and the width W is approximately 0.027". Thus, the shoulder 226 effectively functions as a stop when the hex-shaped distal end 224 of the driver is inserted into the mating cavity of the implant's threaded screw. The shoulder 226 and the cavity desirably include complementary chamfers 228, to permit easier entry of the hex-shaped distal end 224 into the cavity of the implant's threaded screw.

The illustrated torque wire 86 may include one or more reduced-diameter portions 230 on a proximal side of the shoulder 226. The diameter of portion 230 may be smaller than both the width of the shoulder 226 and a diameter of a main portion 232 of the torque wire 86, which in one embodiment extends from the proximal end of reduced-diameter portion 230 to the proximal end 222 of the torque wire 86. In one embodiment, as can be better understood with reference to FIG. 18, the main portion 232 of the torque wire 86 has a diameter in the range of about 0.009" to about 0.020". The reduced-diameter portion 230 may have a length of approximately 0.5" or more and a diameter in the range of about 0.008" to about 0.018". In another embodiment, the diameter of the reduced-diameter portion is greater than about 0.010". As illustrated in FIG. 16, the inside diameter of the torque sheath 84 is large enough to permit the torque wire 86 to rotate within the torque sheath 84 lumen. In one embodiment, the diameter of the torque sheath 84 lumen is equal to the outside diameter of the torque wire 86 plus a tolerance of at least about an additional 0.002" or more. However, other suitable dimensions may also be employed. Desirably, each of the transitions between the reduced-diameter portion 230 and the main portion 232 of the torque wire 86 and the transition between the reduced-diameter portion 230 and the shoulder 226 define a chamfer 234, 236, respectively to advantageously reduce stress concentrations.

Figure 20:
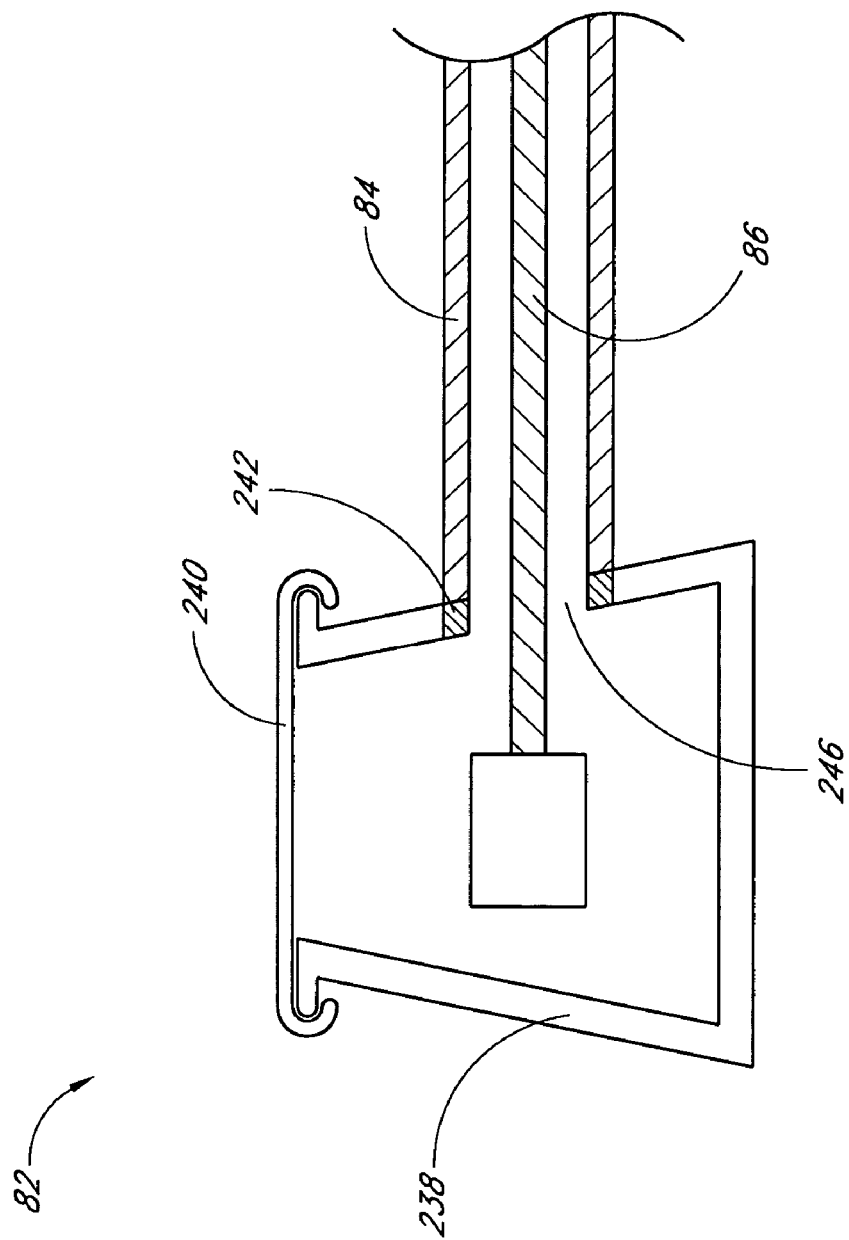
FIG. 20 is a cross-sectional schematic view of an implantable connector housing in accordance with one embodiment of the present invention.

Referring now to FIG. 20, there is schematically illustrated an implantable housing 82 according to one embodiment of the present invention. The implantable housing 82 includes a frame 238, a cover 240, and a torque sheath coupling 242. The implantable housing 82 may also include a gearbox 244 (see FIG. 21). The implantable housing 82 is dimensioned to be implanted subcutaneously within the patient, such as near the entry site into the patient's vasculature through which an implant is to be delivered.

The frame 238 of the implantable housing 82 is generally made from a biocompatible material, such as stainless steel, titanium, or an implantable polymer. The frame 238 may have a trapezoidal cross-sectional profile, such as illustrated in FIG. 20, although any of a variety of shapes may be selected. The shape of the frame 238 will be selected by those of skill in the art to facilitate subcutaneous implantation, and will depend upon the location of implantation. The frame may include holes, tissue ingrowth materials, or other structures to facilitate immobilization during implantation. Immobilization may occur by using sutures or as a result of tissue ingrowth.

The frame 238 includes a torque sheath coupling 242 to which the torque sheath 84 is attached. The torque sheath coupling 242 may be any permanent or releasable bond or joint known to those of skill in the art for attaching the torque sheath 84 to the frame 238. For example, the torque sheath coupling 242 may be a weld, an adhesive, a chemical bond, a thermal bond, a mechanical bond, a compression fitting, a press fitting or a threaded or keyed fitting, as will be understood by those of skill in the art. The torque sheath coupling 242 provides a passage 246 through which the torque wire 86 or other control wire extends and enters the inside of the implantable housing's frame 238. The torque sheath coupling 242 attaches to the torque sheath 84 such that bodily fluid does not enter the implantable housing 82. In addition, the torque sheath coupling 242 prevents the torque sheath 86 from rotating with respect to the frame 238 as the torque wire 84 is rotated with respect to the frame 238.

In one embodiment, the proximal end of the torque wire 84 is attached to a first gear 248, as illustrated in FIG. 21. The first gear 248 is engaged with a second gear 250, such that rotation of the second gear 250 causes the first gear 248 to rotate as well. First and second gears 248, 250 are generally oriented at 90° to one another, but may be oriented at other angles, as is well known to those of skill in the art. In one embodiment, the second gear 250 includes a driver port 252 into which a tool 254 (not shown) may be inserted.

The distal portion of one embodiment of a tool 254 suitable for use with the present invention is illustrated in FIG. 22. The tool 254 has a non-circular cross-sectional shape, and may be inserted into the driver port 252 of the second gear 250 (illustrated in FIG. 21). In one embodiment, the cross-sectional shape of the tool 254 is hexagonal, as illustrated in FIG. 23. However, it will be well understood by those in the art that the tool 254 may have any of a variety of non-circular cross-sectional shapes, including triangular, square, rectangular, elliptical, torx, star, etc. In one embodiment, the tool 254 has a handle (not shown), which when turned causes the second gear 250 to rotate. The handle (not shown) may include a motor and an energy source. As the second gear 250 rotates, its gears or threads cause the first gear 248 to rotate as well. As the first gear 248 rotates, the torque wire 86 is rotated, thereby remotely affecting the shape of the implant (not shown) as discussed above.

The tool 254 may be made from a variety of materials suitable to deliver sufficient torque to the second gear 250 and cause the torque wire 86 to rotate. In one embodiment, the tool is made from stainless steel, aluminum, titanium, or plastic. The tool 254 may have an alignment tip 256, such as a chamfer, for facilitating alignment and insertion of the tool 254 into the driver port 252 of the second gear 250. In one embodiment the alignment tip 256 has a circular cross-sectional area, while the portion of the tool 254 substantially adjacent the alignment tip 256 has a non-circular cross-sectional area. The tip 256 may be adapted for piercing a membrane, such as membrane 240. In another embodiment, the tip 256 is a non-coring piercing tip, as is well known to those of skill in the hypodermic needle arts.

Referring back to FIG. 20, the cover 240 of the implantable housing 82, may be removably or permanently attached to the implantable housing 82 frame 238. The cover 240 provides a fluid-flow resistant seal, and helps keep bodily fluid and tissue from entering the implantable housing 82. In one embodiment, the cover 240 is an elastomeric cap, although the cover 240 may also be a cover, lid, or other structure that may be removed or opened to expose the connector. Alternatively, the cover 240 may comprise a pierceable membrane or septum, that may be pierced by an adjustment tool such as a tool 254.

In one embodiment, the implantable housing 82 is configured to lie beneath the skin, and is palpable so that the cover 240 can be tactually located. The cover 240 may include a membrane that can be pierced and penetrated by, a needle, probe or tool 254, as discussed above. In another embodiment, the physician locates the cover 240, and makes an incision in the patient's skin so that the cover 240 may be peeled back, opened or otherwise removed. Once removed, the physician can insert a tool 254 into the implantable housing 82 such that the tool 254 engages the proximal end of the control wire such as via gearbox 244. Once engaged, rotating the tool 254 will remotely adjust the shape of the implant, as described in greater detail above.

Figure 24:
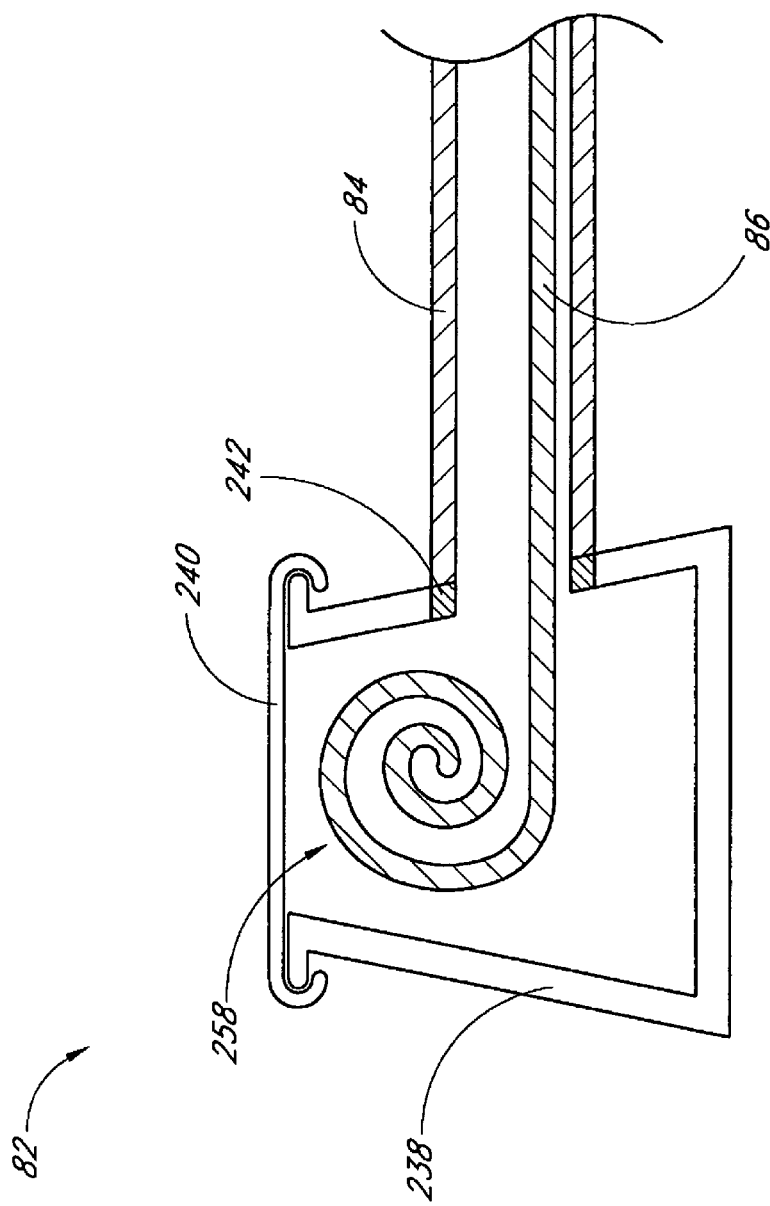
FIG. 24 is a cross-sectional schematic view of another embodiment of an implantable connector housing, where the proximal end of the torque wire is placed in a coil.
Figure 27:
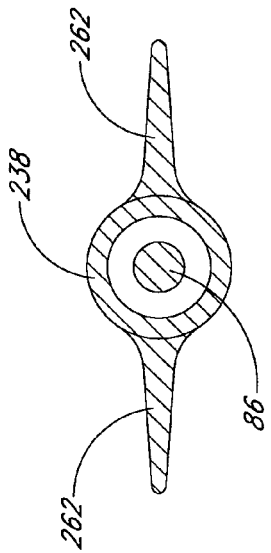
FIG. 27 is a cross-sectional view of the implantable housing of FIG. 26 taken along line 27-27.
Figure 28:
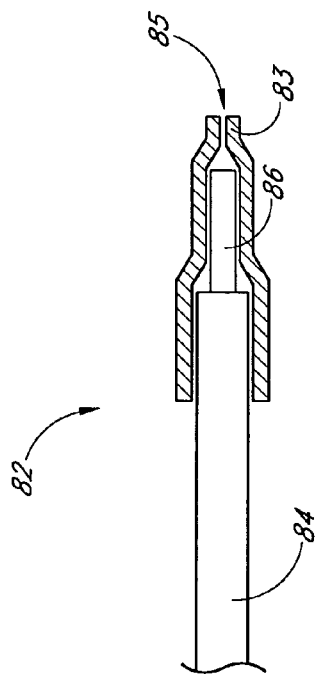
FIG. 28 is another embodiment of an implantable connector, including a male connector on the rotational core, covered by a boot.

Another embodiment of the implantable housing 82 is illustrated in FIG. 24. The implantable housing of FIG. 24 also includes a frame 238, a cover 240, and a torque sheath coupling 242. However, the proximal end of the torque wire 84 is wrapped into a coil 258, instead of coupling to a gearbox 244. In such embodiment, the shape of the implant (not shown) may be remotely affected by accessing the coil 258 after accessing and removing the cover 240, and then applying torque directly to the torque wire 84. Various handpieces may be used to apply such torque to the torque wire 84, as is well known to those of skill in the art.

One embodiment suitable for use with the motorized implants of FIGS. 8 and 9 is illustrated in FIG. 25. In the illustrated embodiment, at least one electrically conductive lead 140 travels proximally through a tubular sheath 86, and is coupled to an implanted electrical connector 258 located within the implantable housing 82. The implanted electrical connector 258 contains at least one contact 260, sometimes two contacts, and in several embodiments, more than two contacts. The number of contacts 260 will vary based upon the number of conductors (not shown) carried by the lead 140. An electrical energy source (not shown) couples through an external electrical connector 261 with the implanted electrical connector 258 such that electrical energy is delivered to the contacts 260, through the lead 140 conductors, and to the motor of the implant (not shown) thereby remotely affecting the implant shape.

One embodiment of an external electrical connector 261 is illustrated in FIG. 25A. The external electrical connector 261 of FIG. 25A includes a shaft 264, an alignment tip 266, and electrical contacts 268. The tip 266 may be adapted for piercing a membrane, such as membrane 240. In one embodiment, the tip 266 is a non-coring piercing tip, as is well known to those of skill in the hypodermic needle arts. One or more electrical contacts 268 (such as the electrical contacts 268 illustrated in FIG. 25A) conduct energy to the electrical contacts 260 during use.

Figure 26:
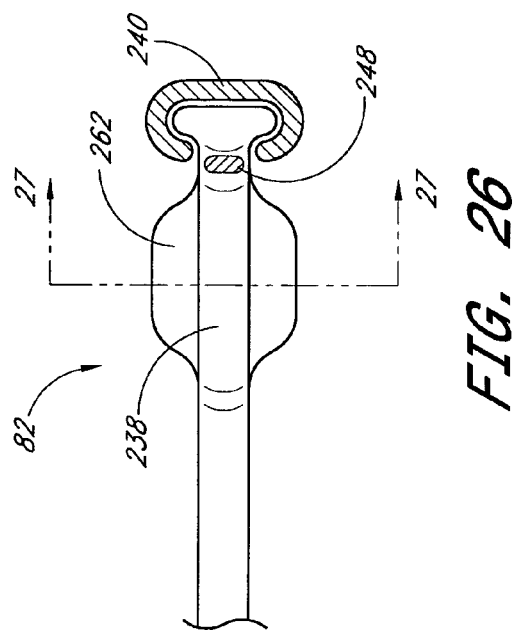
FIG. 26 is another embodiment of an implantable connector housing, including an optional subcutaneous tissue anchor.

Another embodiment of an implantable housing is illustrated in FIG. 26. The illustrated embodiment of an implantable housing 82 contains two anchors 262, which may be integrally formed as part of the implantable housing 82 frame 238. The anchors 262 may be wing-like projections, suitable for implantation beneath the patient's skin, which resist migration of the implantable housing 82 once implanted. The implantable housing 82 may also include a cover 240 which may be removed to expose a control wire.

Alternatively, the housing 82 may take the form of a polymeric boot or cap 83 which seals the proximal end of the tubular sleeve 84. See FIG. 28. Boot 83 may be an elastomeric cap, formed from silicone, latex or other elastomeric material. Alternatively, boot 83 may comprise a rigid polymeric cap, which is snap fit or friction fit onto the distal end of tubular sleeve 84.

Once accessed by the physician, the boot 83 may be removed to expose the torque wire 86. Alternatively, in an elastomeric boot embodiment, the boot may be left in place secured to the distal end of tubular sleeve 84 while an adjustment tool is advanced through optional pilot hole 85 in the boot, to engage the torque wire 86. Following adjustment, the tool may be removed by proximal retraction through the pilot hole 85, which will reclose to provide a seal due to its elastic properties.

Figure 29:
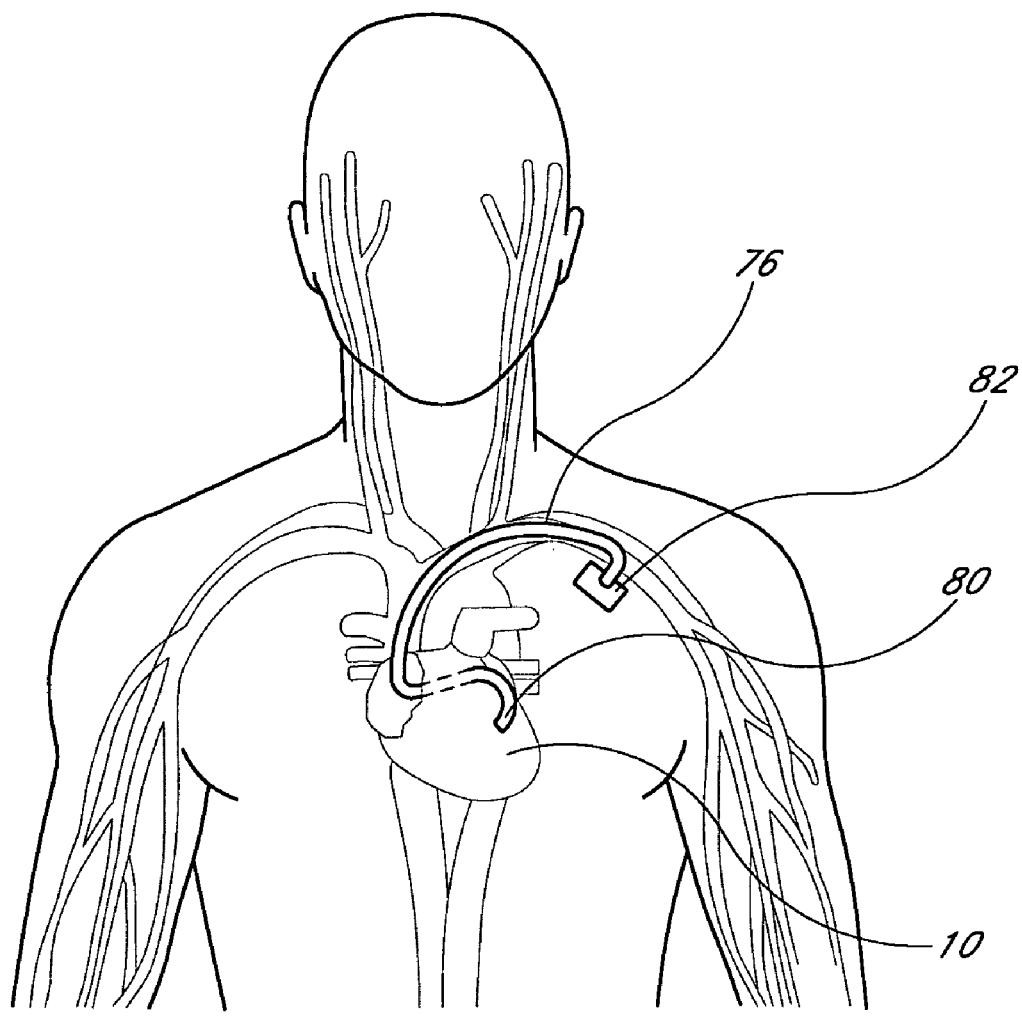
FIG. 29 is a schematic representation of the human circulatory system in a patient after percutaneous delivery of a mitral annuloplasty device to the heart via the superior vena cava.

Referring now to FIG. 29, there is illustrated a simplified schematic view of the human circulatory system through which one embodiment of the present invention is provided. An implant 80 is delivered to the coronary sinus of the heart 10 in order to affect the shape of the mitral valve annulus, as described in greater detail above. The implant 80 is coupled to a tether 76, which includes a torque wire and torque sheath. Prior to implantation, tether 76 and implant 80 are loaded onto a catheter (not shown). In the illustrated embodiment, the physician makes an incision in the patient's skin near the shoulder in order to access the patient's vasculature such as the internal jugular vein, although the subclavian vein, auxiliary vein, or any other such suitable vein as is well known to those of skill in the art, may be used. The physician steers, guides, or directs the catheter through the vasculature, and enters the heart through the superior vena cava 14 (as illustrated in FIGS. 1 and 2). From the superior vena cava 14 the catheter is guided into the coronary sinus 22, as described in greater detail above.

Once the catheter is properly positioned, the implant 80 is deployed, and the implant 80 shape is remotely adjusted by manipulating the proximal end of the tether 76 or a separate adjustment element on the deployment catheter. In one embodiment, the proximal end of the tether 76 is manipulated by rotating the torque wire with respect to the torque sheath, as described in greater detail above. Once the desired implant 80 shape is achieved, the catheter is retracted and removed from the patient's vasculature. Once the catheter is removed, the implant is left inside of the heart 10 and is coupled to the tether 76, which remains inside of the patient's vasculature, exiting the patient's body at the incision. The proximal end of the tether 76 may then be coupled to an implantable housing 82 according to any of the embodiments described above.

To couple the tether 76 to the implantable housing 82, the torque wire may be introduced into the implantable housing through a passage 246 (not shown), such as described above with respect to FIG. 20. The torque sheath is coupled to the implantable housing 82 with a torque sheath coupling 242, such as described above with respect to FIG. 20. The torque wire may be coupled to a gearbox or placed as a coil within the implantable housing 82, such as described above.

Figure 30:
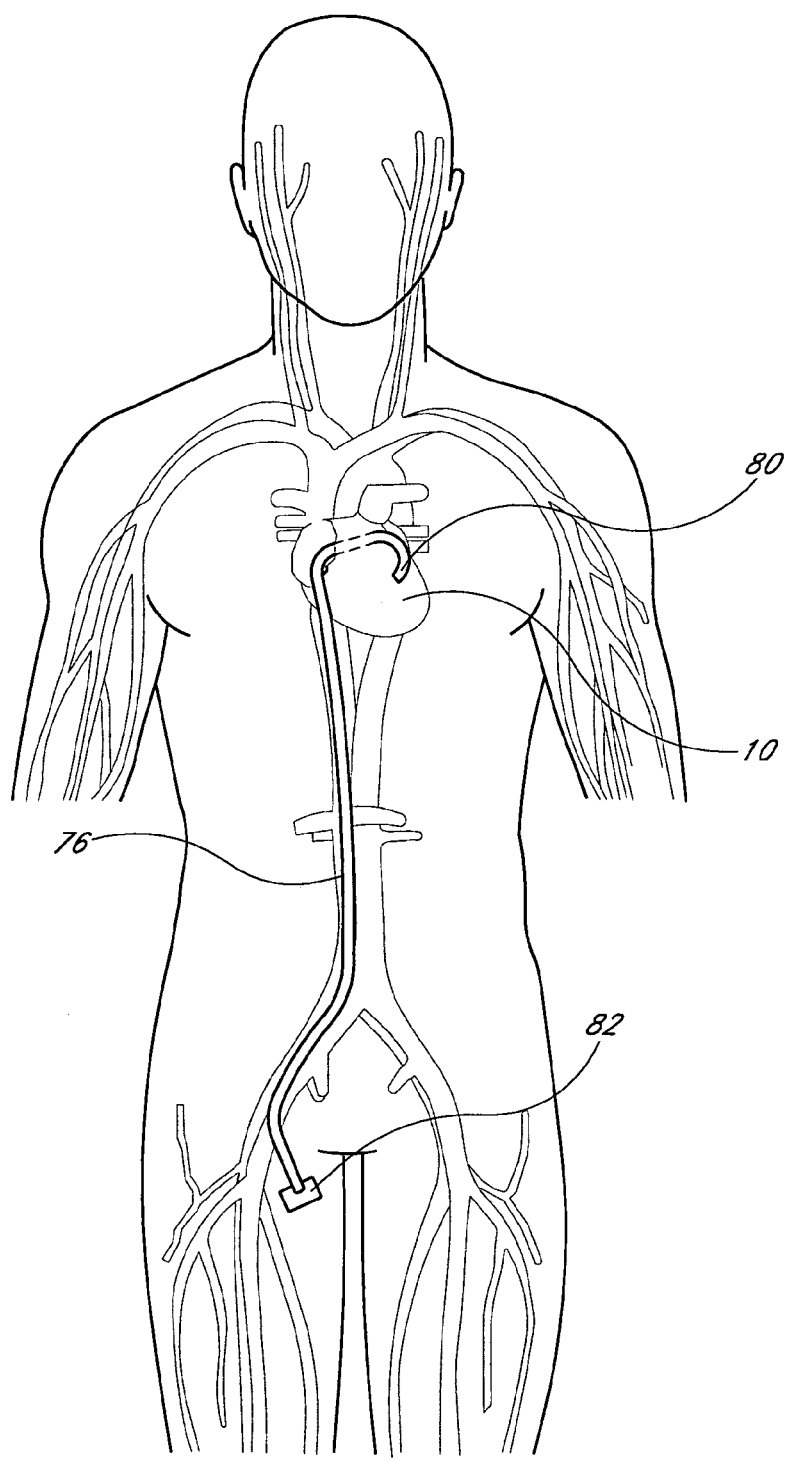
FIG. 30 is a schematic representation of the human circulatory system in a patient after percutaneous delivery of a mitral annuloplasty device to the heart via the inferior vena cava.

An inferior vena cava access route is illustrated in the embodiment of FIG. 30. The embodiment of FIG. 30 is similar to that of FIG. 29, except that in the incision to access the vasculature is made below the heart. In one embodiment, the incision is made near the internal or external iliac, femoral, or popliteal veins. The access incision may be made at a variety of locations suitable for accessing a patient's vasculature. As in FIG. 29, the implant 80 is delivered to the heart 10 by a catheter which travels through the vasculature, enters the heart 10 through the inferior vena cava 16, from which the coronary sinus 22 is reached.

As described above, the tether 76 may be permanently mounted to the implant, or may be mounted thereto during the course of the procedure. In embodiments in which the tether 76 is permanently mounted to the implant, the tether 76 may extend parallel to the delivery catheter, either within a lumen extending axially through the delivery catheter or on the outside of the delivery catheter. Following implantation and initial adjustment with the delivery catheter, the delivery catheter may be proximally withdrawn leaving the tether in place.

Alternatively, the tether 76 may be connected to the implant following the initial positioning of the implant step. This may be accomplished by advancing the tether 76 through a lumen in the deployment catheter, for attachment such as by rotation, snap fit or other connection to the implant. In a further variation, an exchange catheter may be advanced distally inside or outside of the deployment catheter for connection to the implant. Following connection of the exchange catheter to the implant, the deployment catheter may be decoupled from the implant and proximally removed, leaving the exchange catheter in position. The tether 76 may thereafter be advanced through or along the exchange catheter, and connected to the implant in situ. The exchange catheter may thereafter be decoupled from the implant, and proximally withdrawn from the patient, leaving the implant having a tether 76 connected thereto.

Once the implant and tether have been implanted, the implantable housing 82 (e.g., the housing 82 of FIGS. 20, 24, 25, 26, and 28) may be subcutaneously buried or implanted as well. It is well understood by those of skill in the art that depending upon the particular housing employed, the housing may be implanted before, during or after implant and tether implantation. The housing 82 is coupled to the tether 76, as described in greater detail above. In one embodiment, a cover 240 is provided to maintain a fluid-flow resistant seal, keeping bodily fluid and tissue from entering the housing 82. The housing 82 is buried within the patient's tissue near the access point, as is well known to those of skill in the art.

If subsequent clinical monitoring reveals that implant adjustment is indicated, a physician may open the access point and retrieve the housing. Such monitoring may occur hours, days, months, or years after the initial implantation of the implant, tether, and housing. Once retrieved, the physician may adjust the implant shape or position, by removing or piercing the cover with an appropriate tool, and engaging the proximal end of the control wire, as described in greater detail above. In one embodiment, the physician adjusts the implant while using hemodynamic monitoring to assess the affects of implant adjustment. Once the indicated adjustments have been made, the physician may re-bury the housing for subsequent adjustments, as may be required.

Implants in accordance with the present invention may be utilized throughout a wide variety of other medical indications. For example, the implant may be modified for use in applying compressive force to other valves in the heart. Modified embodiments of the device may be placed adjacent or around the left ventricle of the heart, such as to assist CHF patients. The device may be positioned in the vicinity of any of a variety of natural sphincter muscles, such as the lower esophageal sphincter to treat gastroesophageal reflux disease. The implant may be positioned in the vicinity of the pylorus, or elsewhere on the stomach for use in the treatment of obesity. Modified versions of the implant disclosed herein may be positioned in the vicinity of a nerve, such that pressure may be selectively applied to the nerve to affect the transmission of pain or other signals. The implant may also be modified for use in applying compressive force to the urethra.

The present invention has been described in terms of certain specific embodiments. However, changes and variations on the foregoing will become apparent to those of skill in the art in view of the disclosure herein. Accordingly, the invention is not intended to be limited by the foregoing embodiments, but rather by the full scope of the attached claims.

What is claimed is:

1. A method of treating a patient, comprising the steps of:
   identifying a patient having an implant residing within the patient, wherein the implant comprises an associated connector, and an elongate flexible tubular sleeve connecting the connector to the implant, wherein the elongate flexible tubular sleeve has at least one control line therein, the at least one control line extending from the connector to the implant;
   after identifying the patient, the method further comprising:
   removing a cover over the connector;
   accessing the connector;
   connecting an adjustment tool to the connector, the adjustment tool located at least partially outside the patient's body; and
   actuating the adjustment tool to adjust an amount of force, exerted by at least a portion of the implant against adjacent tissue, from a first force to a second force;
   wherein actuating the adjustment tool comprises rotating the adjustment tool in a first direction within the connector and changing the direction of rotation, within the connector, to drive the at least one control line in a second direction of rotation, different than the first direction,
   wherein, after the actuating of the adjustment tool, and after the adjustment tool is entirely outside the patient's body, the connector remains connected to the implant by the tubular sleeve, the at least one control line remains extending from the connector to the implant, and the at least a portion of the implant continues to exert substantially the second force against the adjacent tissue.

2. A method of treating a patient as in claim 1, wherein the actuating step adjusts force against a heart valve.

3. A method of treating a patient as in claim 2, wherein the actuating step adjusts force against the annulus of the mitral valve.

4. A method of treating a patient as in claim 3, wherein the actuating step adjusts the position of the posterior leaflet of the mitral valve.

5. A method of treating a patient as in claim 1, wherein the actuating step adjusts force against a natural body lumen.

6. A method of treating a patient as in claim 1, wherein the actuating step adjusts force against the lower esophageal sphincter.

7. A method of treating a patient as in claim 1, wherein the actuating step adjusts force against the stomach.

8. A method of treating a patient as in claim 1, wherein the actuating step adjusts force against the urethra.

9. A method of treating a patient as in claim 1, wherein the actuating step adjusts force against a nerve.

10. A method of treating a patient as in claim 1, wherein the actuating step is accomplished at least ten minutes following implantation of the implant into the patient.

11. A method of treating a patient as in claim 10, wherein the actuating step is accomplished at least 24 hours following implantation of the implant into the patient.

12. A method of treating a patient as in claim 11, wherein the actuating step is accomplished at least two weeks following implantation of the implant into the patient.

13. A method of treating a patient as in claim 1, further comprising the step of measuring an indicium of the patient's condition prior to the actuating step.

14. A method of treating a patient as in claim 1, additionally comprising the step of monitoring hemodynamic function.

15. A method as in claim 14, wherein the monitoring step is accomplished using transesophageal echocardiography.

16. A method as in claim 14, wherein the monitoring step is accomplished using surface echo cardiographic imaging.

17. A method as in claim 14, wherein the monitoring step is accomplished using intracardiac echo cardiographic imaging.

18. A method as in claim 14, wherein the monitoring step is accomplished using fluoroscopy with radiocontrast media.

19. A method as in claim 14, wherein the monitoring step is accomplished using left atrial or pulmonary capillary wedge pressure measurements.

20. A method as in claim 14, further comprising the step of determining an ongoing drug therapy taking into account hemodynamic function.

21. A method as in claim 1, comprising measuring residual regurgitation following the actuating step and formulating an ongoing drug therapy taking into account the residual regurgitation.

22. A method as in claim 1, wherein the control line is coupled to the implant proximate to the implant's distal end.

23. A method as in claim 1, wherein changing the direction of rotation within the connector comprises engaging and rotating, with the adjustment tool, a gear located within the connector.

24. A method, of treating a patient, comprising:
identifying a patient having a control line coupled to an implant that resides in the patient, the control line extending through a tubular sleeve that extends from the implant to a housing implanted at a site in the patient that is remote from the implant, the implant exerting, in a first configuration, a first pressure on an extravascular target site within the patient;
accessing, with an access device located at least partially within the body, the control line, via the implanted housing, at the site; and
transmitting energy, with the access device, through the control line, to a motor, located with the implant, that changes, upon receipt of the transmitted energy, the implant from the first configuration to a second configuration, thereby adjusting a pressure, exerted by the implant, to a second pressure, different from the first pressure;
wherein, after the transmitting energy through the control line and after removing the access device from the body, the control line remains coupled to the implant and extends from the implant to the housing through the tubular sleeve, and the implant maintains exertion of substantially the second pressure on the extravascular target site.

25. A method as in claim 24, wherein the implant is intravascular within the patient.

26. A method as in claim 24, further comprising penetrating the patient's skin from outside the body with the access device, after the identifying of the patient and before the transmitting energy through the control line.

* * * * *